(12) United States Patent
Javed et al.

(10) Patent No.: US 8,097,460 B2
(45) Date of Patent: Jan. 17, 2012

(54) **ETHANOL PRODUCTION IN *BACILLUS***

(75) Inventors: Muhammed Javed, Dagenham (GB);
Fiona Cusdin, Horley (GB); Paul Milner, Ickenham (GB); Edward Green, Guildford (GB)

(73) Assignee: Elsworth Biotechnology Limited, Surrey (GB)

( * ) Notice: Subject to any disclaimer, the term of this patent is extended or adjusted under 35 U.S.C. 154(b) by 0 days.

(21) Appl. No.: 12/391,366

(22) Filed: Feb. 24, 2009

(65) Prior Publication Data

US 2010/0190259 A1    Jul. 29, 2010

Related U.S. Application Data

(63) Continuation of application No. 11/108,870, filed on Apr. 19, 2005, now abandoned, which is a continuation of application No. 09/971,361, filed on Oct. 5, 2001, now abandoned.

(60) Provisional application No. 60/247,017, filed on Nov. 13, 2000.

(30) Foreign Application Priority Data

Oct. 6, 2000    (GB) .................................. 0024554.8

(51) Int. Cl.
*C12N 15/87* (2006.01)
*C12N 15/82* (2006.01)
*C12N 9/06* (2006.01)
*C12N 9/04* (2006.01)
*C12N 15/00* (2006.01)
*C12N 1/21* (2006.01)
*C12P 21/00* (2006.01)
*C07H 21/00* (2006.01)

(52) U.S. Cl. ........ 435/463; 435/471; 435/190; 435/191; 435/69.1; 435/320.1; 435/252.31; 536/23.2

(58) Field of Classification Search .................. 435/161, 435/69.1, 463, 471, 190, 191, 325, 252.3, 435/252.31; 530/350; 536/23.2
See application file for complete search history.

(56) References Cited

U.S. PATENT DOCUMENTS 5,482,846 A    1/1996  Ingram

FOREIGN PATENT DOCUMENTS

| EP | 603 416 A1 | 6/1994 |
| EP | 414 297 A1 | 2/1997 |
| EP | 761 815 A2 | 3/1997 |
| EP | 087559 | 11/1998 |
| WO | WO 01/49865 | 7/2001 |

OTHER PUBLICATIONS

Deng & Coleman, "Ethanol Synthesis by Genetic Engineering in Cyanobacteria," Applied Env. Microbiol. 65, 523-28, Feb. 1999.

Ingram et al., "Metabolic engineering of bacteria for ethanol production," Biotechnol. Bioengin. 58, 204-14, Apr. 1998 (abstract).

Lessard et al., "Expression of genes encoding the E2 and E3 components of the *Bacillus stearothermophilus* pyruvate dehydrogenase complex and the stoichiometry of subunit interaction in assembly in vitro," Eur. J. Biochem. 258, 491-501, Dec. 1998 (abstract).

Lowe et al., "Dual role of a single multienzyme complex in the oxidative decarbosylation of pyruvate and branched-chain 2-oxo acids in *Bacillus subtilis*," Biochem. J. 215, 133-40, 1983.

Sakoda & Imanaka, "Cloning and Sequencing of the Gene Coding for Alcohol Dehydrogenase of *Bacillus sterothermophilus* and Rational Shift of the Optimum pH," J. Bacteriol. 174, 1397-1402, Feb. 1992.

Waldvogel et al., "Structure and function of L-lactate dehydrogenases from thermophilic and mesophilic bacteria. VII. Nucleotide sequence of the lactate dehydrogenase gene from the mesophilic bacterium *Bacillus megaterium*. Preparation and properties of a hybrid lactate dehydrogenase comprising moieties of the B. megaterium and B. stearothermophilus enzymes," Biol. Chem. Hoppe Seyler 368, 1391-99, Oct. 1987 (abstract).

Zülli et al., "Structure and function of L-lactate dehydrogenases from thermophilic and mesophilic bacteria. VI. Nucleotide sequences of lactate dehydrogenase genes from the thermophilic bacteria *Bacillus stearothermophilus, B. caldolyticus* and *B. caldotenax*," Biol. Chem. Hoppe Seyler 368, 1367-77, Sep. 1987 (abstract).

GenBank Accession No. M19394, sequence of *B. caldolyticus* lactate dehydrogenase gene (strain DSM 405), disclosed in Zülli et al., "Structure and function of L-lactate dehydrogenases from thermophilic and mesophilic bacteria. VI. Nucleotide sequences of lactate dehydrogenase genes from the thermophilic bacteria *Bacillus stearothermophilus, B. caldolyticus* and *B. caldotenax*," Biol. Chem. Hoppe Seyler 368, 1367-77, Sep. 1987.

GenBank Accession No. M19395, sequence of *B. caldotenax* lactate dehydrogenase gene (strain DSM 406), disclosed in Zülli et al., "Structure and function of L-lactate dehydrogenases from thermophilic and mesophilic bacteria. VI. Nucleotide sequences of lactate dehydrogenase genes from the thermophilic bacteria *Bacillus stearothermophilus, B. caldolyticus* and *B. caldotenax*," Biol. Chem. Hoppe Seyler 368, 1367-77, Sep. 1987.

GenBank Accession No. M19396, sequence of *B. stearothermophilus* lactate dehydrogenase gene, disclosed in Zülli et al., "Structure and function of L-lactate dehydrogenases from thermophilic and mesophilic bacteria. VI. Nucleotide sequences of lactate dehydrogenase genes from the thermophilic bacteria *Bacillus stearothermophilus, B. caldolyticus* and *B. caldotenax*," Biol. Chem. Hoppe Seyler 368, 1367-77, Sep. 1987.

(Continued)

Primary Examiner — Delia Ramirez
(74) Attorney, Agent, or Firm — Banner & Witcoff, Ltd.

(57) ABSTRACT

The present invention relates to the production of ethanol as a product of bacterial fermentation. In particular this invention relates to a novel method of gene inactivation and gene expression based upon homologous recombination. The method is particularly useful in connection with species of *Bacillus* such as *B. stereothermophilus, B. calvodelox, B. caldotenax, B. thermoglucosidasius, B. coagulans, B. licheniformis, B. thermodenitrificans*, and *B. caldolyticus*.

7 Claims, 17 Drawing Sheets

OTHER PUBLICATIONS

Branden et al., *Introduction to Protein Structure*, Garland Publishing Inc., NY, p. 247, 1991.

I. Biswas et al., Journal of Bacteriology (1993) vol. 175, No. 11, pp. 3628-3635, "High-Efficiency Gene Inaction and Replacement System for Gram-Positive Bacteria".

Lapierre et al., Applied and Environmental Microbiology 65(9):4002-4007, Sep. 1999.

Witkowski et al., Biochemistry 38:11643-11650, 1999.

Broun et al., Science 282:1315-1317, 1998.

Seffernick et al., J. Bacteriol. 183(8):2405-2410, 2001.

Fig. 1
LDH, Insertion Sequence (underlined) and LP gene sequences

```
   1  AGGGCAATCT GAAAGGAAGG GAAAATTCCT TTCGGATTGT CCTTTTAGTT
  51  ATTTTTATGG GGAGTGAATA TTATATAGGC ATTACGGAAA TGATAATGGC
 101  AGAGTTTTTT CATTTATTAG ACTGCTTGAT GTAATTGGAT GTGATGATAC
 151  AAAAATAATG TTGTGTAAAC AAAATGTTAA CAAAAAAGAC AAATTTCATT
 201  CATAGTTGAT ACTTGATAAA GATTGTGAAA TAATGCACAA TATATCAATG
 251  TATGAGCAGT TTCACAAATT CATTTTTTGG AAAGGATGAC AGACAGCGAT
 301  GAAACAACAA GGCATGAATC GAGTAGCACT TATAGGAACG GGGTTCGTTG
 351  GGGCCAGCTA TGCATTTGCC CTTATGAACC AAGGAATAGC AGATGAGTTA
 401  GTATTGATTG ATGTAAATAA GAATAAGGCA GAGGGCGATG TGATGGATTT
 451  AATCACGGAA AAGTATTCGC GCCGAAGCCG ATGAATATTT GGTTTGGAGA
 501  TTATCAAGAT TGCCAAGACG CCGATTTGGT GGTGATTTGT GCAGGGGCTA
 551  ACCAAAAGCC GGGAGAAACA AGACTGGATC TTGTTGACAA AAATATTAAT
 601  ATCTTCAAAA CGATTGTCGA TTCTGTGATG AAATCCGGAT TTGATGGCGT
 651  TANGTCTTGT TGTAAATTAT CACTTTATTT CCGCACAAAA AAGACTCTTT
 701  TTTGCACATT CCTTCGGAAT ATCCCTCTCC CCCTTTCCGA AGAATGTGC
 751  TAAATTTTTT GTGAATTATT TCGGAATGGG ACATGGGTGA TTTCCAGAGG
 801  GGGGACGAGG ACGTGATTCG GTTTCATGAC TTTCAGGTCG ATGTCCAGAC
 851  ATATGCCCAG CGGGGAAAAC AAAACGACTT TCCCCTTCTT AAGCGGTGCC
 901  CTCATTGCCA GGCAAAACGC CCTCTTTATC GCCATGGGTA CTACGAACGA
 951  AATGCCGTGA CGTCGCATCA GTCTTATCGC ATTTGGATCG CTCGGTATCG
1001  CTGCCCGGAG TGCAGGAGGA CGGTGGCCGT GTTGCCTTCA TTTCTTCTCC
1051  CTTATTTTCA GTATACGTTG CCCACCATAT GGAGAGTGGT GAAAGAACGG
1101  TTGGGCCTGA CTCCGAAACG GGGGATGGAG GAGGCTCCAC TCCTTCCTAC
1151  GGATGAAGGG GTTTTATTTT ATGTCCCGAC GTTTATTCCG AAATTTGAAC
```

Fig. 1 (contd.)

```
1201  CACCTTCATT GGTTTTTTGC GGAGCGCTGG GAGAAAAATT GGTCCTGCCA
1251  TCGCCCAAGC CGAGAGAACG AGCCCTATGG TGGATCCAGA CGATGGAGGA
1301  GATCGGCCTC TTTTTCGTCA TCCAAGAGAT ATGGGAGCAC CGATCGACGC
1351  ATCTTTTTGC ACGTACATTC AGTTCCTGAT TTACTTATAT CCCCTTATAT
1401  GGAATCATTT ATAGATTCCC AAACCTTTCC TCTCGACGGT CGGGGGAATG
1451  ATCCGATAGG ATAGAGACAG GATGGACCGA TAAGGTCCTA GAATGGGATG
1501  AACGAAGGAG GAGATCGAAA TGAATGAGTC GATGAGACAG GAGATCGCTT
1551  TATTTCGGTA TGGATTGATC GCTCCATTGG TGAATGGACA AGTCGATCCA
1601  AAAACGTACT TGAAGGAAGT AGCGGAACGG ATCCATCAAG TTCCCCACCA
1651  TGGAGAGAAA CGCATCGCCG CCAAAACGAT CCTCGACTGG TGCACGCAGT
1701  ACAAAAAAGG GGGCTTTGAG GCGCTGAAGC CGAAACGACG GTCGGACCGT
1751  GGCCATTCCC GGAGGCTGTC ACCTGAAGAA GAGGATCACA TTTTAGCCCT
1801  GAGAAAAAAA CACCCCCACA TGCCCGTGAC GGTGTTTTAC CAACACCTTA
1851  TCGAGCAGGG GGAAATCCAA TCCATCTCTT ATTTCACTAT ATACCGACTT
1901  TTAAAAAAAT ACAACCTCGT GGGGAAAGAA ATTTTACCGA TTCCTGAACG
1951  AAAACGATTC GCGTACGATC AGGTCAATGA GCTCTGGCAA GGTGATTTGT
2001  CCCATGGCCC GTTGATTCGC GTGAATGGCA AAACGCAAAA AACGTTTTTG
2051  ATTGCCTATA TCGATGACTG CTCGCGGGTC GTGCCGTACG CTCAGTTTTT
2101  CTCTTCCGAG AAATTTGACG GGTTGCGGAT CGTAACCAAG GAAGCGCTGC
2151  TTCGATACGG AAAGCCGAAG CGAATTTACT CGGATAACGG CAAGATTTAT
2201  CGGGCGGAAC CCTTGCAGTA CGCCTGCGCG GAGTTAGGGA TCACCTTGAT
2251  CCATACCCAG CCGTACGATC CGCAAAGCAA AGGGAAAATC GAACGATTTT
2301  TCCGCACCGT ACAGACGCGG TTTTACCCGT TGCTCGAAAT GAATTCACCG
2351  AAGTCGCTCG AAGAGCTAAA CGAGCGATTT TGGAAGTGGT TGGAGGAAGA
2401  TTACCATCGA AAACCGCATG CCTCGTTGAA CGGGAAGACG CCACATGAAG
2451  TGTTTCAATC GCAAGTCCAT TTGGTGTCGT TCGTCGAGGA TTCGGATTGG
```

Fig. 1 (contd.)

```
2501  CTCGACTCGA TCTTTTTGAA ACGCGAATAC CGTAAAGTGA AGGCCGATGG
2551  TACGGTCACG TTGAACAAGC AGCTGTATGA AGTTCCGCCC CGGTTCATCG
2601  GACAATCGAT CGAACTCCGT TATGATGAAC AAGGCGTGTA TGTGTACGAA
2651  GACGGTCAAC GGGTCGCCGA AGCGGTCCTT GTTCGCTTCG AGGACAATGC
2701  CTATGTGAAA CGCCATCGGT CACCGTTTGC GGCGGTTCCG GTAGAGGGAG
2751  GCGAAAACGA TGTATAAAAC GTTTTATTCC CTTTCCCGAG AGCCGTTTTC
2801  GAAGGAGACG AATCCACCAG AGGCTTATCA AGGGGCCTCG TATCAAGAGG
2851  CCCTCGCCGC TTTGGACTAC GTGAAACGAA CAAGAGGGAT CGGGCTATTG
2901  ATCGGTGAAC CAGGGGCCGG CAAGACATTC GCCCTTCGGG CGTTTAAGGA
2951  ATCCTGAAT CCGTCACTGT ATCACGTCGT TTATTTTCCA TTGTCAACGG
3001  GAAGCGTGAT GGACTTTTAT CGCGGCCTTG CCTTCGGGCT CGGGGAAGAG
3051  CCGAAATACC GCAAGGTCGA CTTGTTTTAT CAAATCCAAC AAGGGATCGA
3101  GCGCTTGTAT CATGAACAAC GGGTAACGTC AGTGTTCATC CTCGATGAAA
3151  TGCATTTAGC GAAGGATGCC TTTCTGCAGG ATATCGCGAT CCTGTTCAAC
3201  TTTCACATGG ACTCAACAAA TCCGTTTGTC TTGATTTTGG CGGGGCTGCC
3251  CCATTTACAG GCAAAACTAC GGTTGAAATC AACACCGTCC GCTTCACCAA
3301  CGAATCATCA TGCGATACCA GATGGGGCCT CTTGATAAGG AAGAAGTGGT
3351  AGGATATATC GAACACCGCT GAAACAGGCG GGGCGAAAC ACCCGATTTT
3401  TACCCCAGCT GCCTTAGAAG CGATCGCCCT GCAGTCGCAG GGGTGGCCGC
3451  GGATCATCAA CAACCTCGCC ACCACTTGCC TGTTATACGG CGCTCAATTA
3501  AAAAAACATA TGATTGACGA AGACATTGTG CGTATGGCAG CCGAAGAAAT
3551  GGGGTACTGA CACAGCAGGG GCTGATCGGC CCCTGTTATG TTTCATCCCG
3601  ATCCATCCTC ATTCTAGTTA ATCATCCGAA ATAATGTGCA AATGTTCGGA
3651  AATAATCTGC AAAACCTGGA ATAATTCGCA AAGATTTTGC ACATTATTTC
3701  CGAATCCGTC CGAAATAATT TGAAAAAGGG ATTCTGAAAT AATGTGCTAA
3751  TTTACATTTC TTGTGGCAAC GAACCCAGTG GATATTTTAA CGTATGCTAC
```

```
3801  TTGGAAATTT AGCGGGTTAC CGAAAGAGCG GGTAATCGGC TCAGGAACGA
3851  TTCTTGATAC AGCAAGATTC CGCTTCTTGC TAAGTGAATA TTTTCAAGTG
3901  GCTCCGACCA ATGTACATGC GTATATTATT GGCGAGCATG GGGATACAGA
3951  GCTGCCTGTT TGGAGCCATG CGGAAATTGG AAGCATTCCA GTTGAGCAAA
4001  TATTGATGCA AAACGATAAC TATAGAAAAG AGGATTTAGA CAATATCTTT
4051  GTTAATGTTC GTGATGCGGC ATATCAAATC ATTGAGAAAA AAGGGGCAAC
4101  GTATTACGGC ATTGCAATGG GATTAGTCCG TATCACTCGT GCTATTTTGC
4151  ACAATGAAAA TGCCATCTTA ACCGTTTCTG CTCATTTGGA CGGCCAATAT
4201  GGCGAACGAA ATGTTTATAT TGGCGTGCCT GCCATTATCA ACCGAAACGG
4251  TATTCGTGAA GTGATGGAAT TGACGCTAAA TGAAACAGAA CAACAACAAT
4301  TCCATCATAG TGTAACTGTA TTAAAAGACA TTCTTTCCCG TTATTTGAT
4351  GATGTAAAAT AATACTGACT TTGAATACAA CAAGGTGAAC ATCGTGTGGA
4401  TACAACATTA CAATCCCTTG CATAACACAT ATCTTTCGGC ATTTATTGCG
4451  GCGTTTCCGA TCGTTTTATT TCTATTATGC TTAACTGTGT TTAGGATGAG
4501  GGGAGTAAAA GCCGCTTTTC TCATTCTTTG TTTTGGTTTA GTAACAGCTG
4551  TTTTGTTTTT CCATATGCCG ATTTCAAAGG CGATTGCTGC GTCCGTCTAT
4601  GGAATCGCAA ACGGTTTATG GCCGATTGGC TATATTGTGA TTATGGCCGT
4651  CTGGCTGTAT AAAATTGCTG TGAAAACGGG GAAATTTGAT ATTATCCGCA
4701  GCAGTATTGC AAACATTTCG GAGGATCAGC GGCTTCAACT GCTGCTCATC
4751  GGCTTTAGCT TTAATGCTTT TTTAGAAGGA GCTGCAGGAT TCGGTGTTCC
4801  GATTGCCATT TCGGCTGCTT TGCTTTCAGA ACTAGGATTT CATCCATTAA
4851  AAGCGGCCGC GCTTTGCTTA ATTGCCAATG CTGCCTCTGG CGCGTTTGGA
4901  GCGATAGGAA TTC
```

*Fig. 1 (contd.)*

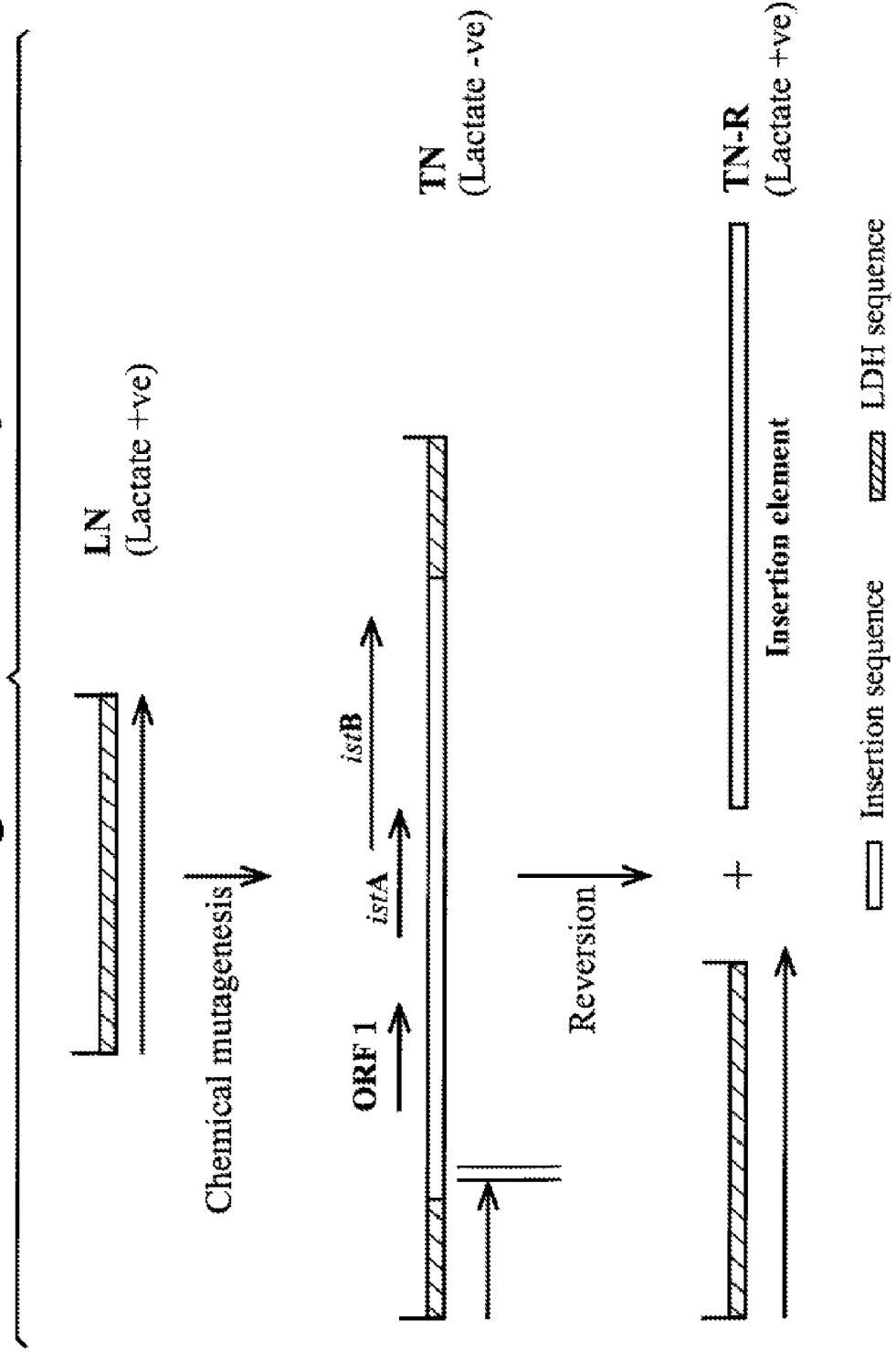
Fig. 2 Genetic Instability of TN

*LDH Gene Inactivation of TN*

Fig. 4 Continuous TN-T9

Figure 6

LDH Sequence from *Bacillus* LN

```
AGGGCAATCTGAAAGGAAGGGAAAATTCCTTTCGGATTGTCCTTTTAGTTATTTTTATGG    - 60
GGAGTGAATATTATATAGGCATTACGGAAATGATAATGGCAGAGTTTTTTCATTTATTAG    - 120
ACTGCTTGATGTAATTGGATGTGATGATACAAAAATAATGTTGTGTAAACAAAATGTTAA    - 180
CAAAAAAGACAAATTTCATTCATAGTTGATACTTGATAAAGATTGTGAAATAATGCACAA    - 240
TATATCAATGTATGAGCAGTTTCACAAATTCATTTTTTGGAAAGGATGACAGACAGCGAT    - 300
                                                          M

GAAACAACAAGGCATGAATCGAGTAGCACTTATAGGAACGGGGTTCGTTGGGGCCAGCTA    - 360
 K  Q  Q  G  M  N  R  V  A  L  I  G  T  G  F  V  G  A  S  Y

TGCATTTGCCCTTATGAACCAAGGAATAGCAGATGAGTTAGTATTGATTGATGTAAATAA    - 420
 A  F  A  L  M  N  Q  G  I  A  D  E  L  V  L  I  D  V  N  K

GAATAAGGCAGAGGGCGATGTGATGGATTTAAATCACGGAAAAGTATTCGCGCCGAAGCC    - 480
 N  K  A  E  G  D  V  M  D  L  N  H  G  K  V  F  A  P  K  P

GATGAATATTTGGTTTGGAGATTATCAAGATTGCCAAGACGCCGATTTGGTGGTGATTTG    - 540
 M  N  I  W  F  G  D  Y  Q  D  C  Q  D  A  D  L  V  V  I  C

TGCAGGGGCTAACCAAAAGCCGGGAGAAACAAGACTGGATCTTGTTGACAAAAATATTAA    - 600
 A  G  A  N  Q  K  P  G  E  T  R  L  D  L  V  D  K  N  I  N

TATCTTCAAAACGATTGTCGATTCTGTGATGAAATCCGGATTTGATGGCGTTTTTCTTGT    - 660
 I  F  K  T  I  V  D  S  V  M  K  S  G  F  D  G  V  F  L  V

GGCAACGAACCCAGTGGATATTTTAACGTATGCTACTTGGAAATTTAGCGGGTTACCGAA    - 720
 A  T  N  P  V  D  I  L  T  Y  A  T  W  K  F  S  G  L  P  K

AGAGCGGGTAATCGGCTCAGGAACGATTCTTGATACAGCAAGATTCCGCTTCTTGCTAAG    - 780
 E  R  V  I  G  S  G  T  I  L  D  T  A  R  F  R  F  L  L  S

TGAATATTTTCAAGTGGCTCCGACCAATGTACATGCGTATATTATTGGCGAGCATGGGGA    - 840
 E  Y  F  Q  V  A  P  T  N  V  H  A  Y  I  I  G  E  H  G  D

TACAGAGCTGCCTGTTTGGAGCCATGCGGAAATTGGAAGCATTCCAGTTGAGCAAATATT    - 900
 T  E  L  P  V  W  S  H  A  E  I  G  S  I  P  V  E  Q  I  L

GATGCAAAACGATAACTATAGAAAAGAGGATTTAGACAATATCTTTGTTAATGTTCGTGA    - 960
 M  Q  N  D  N  Y  R  K  E  D  L  D  N  I  F  V  N  V  R  D

TGCGGCATATCAAATCATTGAGAAAAAAGGGGCAACGTATTACGGCATTGCAATGGGATT    - 1020
 A  A  Y  Q  I  I  E  K  K  G  A  T  Y  Y  G  I  A  M  G  L

AGTCCGTATCACTCGTGCTATTTTGCACAATGAAAATGCCATCTTAACCGTTTCTGCTCA    - 1080
 V  R  I  T  R  A  I  L  H  N  E  N  A  I  L  T  V  S  A  H

TTTGGACGGCCAATATGGCGAACGAAATGTTTATATTGGCGTGCCTGCCATTATCAACCG    - 1140
 L  D  G  Q  Y  G  E  R  N  V  Y  I  G  V  P  A  I  I  N  R

AAACGGTATTCGTGAAGTGATGGAATTGACGCTAAATGAAACAGAACAACAACAATTCCA    - 1200
 N  G  I  R  E  V  M  E  L  T  L  N  E  T  E  Q  Q  Q  F  H

TCATAGTGTAACTGTATTAAAAGACATTCTTTCCCGTTATTTTGATGATGTAAAA        - 1255
 H  S  V  T  V  L  K  D  I  L  S  R  Y  F  D  D  V  K
```

Figure 7A

**Partial Lactate Permease Gene Sequence and Protein Translation from *Bacillus* LN**

```
  1 gtgaacatcgtgtggatacaacattacaatcccttgcataacaca
    V  N  I  V  W  I  Q  H  Y  N  P  L  H  N  T
 46 tatctttcggcatttattgcggcgtttccgatcgttttatttcta
    Y  L  S  A  F  I  A  A  F  P  I  V  L  F  L
 91 ttatgcttaactgtgtttaggatgagggagtaaaagccgctttt
    L  C  L  T  V  F  R  M  G  V  K  A  A  F
136 ctcattctttgttttggtttagtaacagctgttttgttttccat
    L  I  L  C  F  G  L  V  T  A  V  L  F  F  H
181 atgccgatttcaaaggcgattgctgcgtccgtctatggaatcgca
    M  P  I  S  K  A  I  A  A  S  V  Y  G  I  A
226 aacggtttatggccgattggctatattgtgattatggccgtctgg
    N  G  L  W  P  I  G  Y  I  V  I  M  A  V  W
271 ctgtataaaattgctgtgaaaacggggaaatttgatattatccgc
    L  Y  K  I  A  V  K  T  G  K  F  D  I  I  R
316 agcagtattgcaaacatttcggaggatcagcggcttcaactgctg
    S  S  I  A  N  I  S  E  D  Q  R  L  Q  L  L
361 ctcatcggctttagctttaatgcttttttagaaggagctgcagga
    L  I  G  F  S  F  N  A  F  L  E  G  A  A  G
406 ttcggtgttccgattgccatttcggctgctttgctttcagaacta
    F  G  V  P  I  A  I  S  A  A  L  L  S  E  L
451 ggatttcatccattaaaagcggccgcgctttgcttaattgccaat
    G  F  H  P  L  K  A  A  A  L  C  L  I  A  N
496 gctgcctctggcgcgtttggagcgataggaatt 528
    A  A  S  G  A  F  G  A  I  G  I
```

*Figure 7B*

Lactate Permease Nucleotide and Amino Acid Sequence from Bacillus LN

```
  1  GTGAACATCGTGTGGATACAACATTACAATCCCTTGCATAACACATATCTTTCGGCATTT
     V  N  I  V  W  I  Q  H  Y  N  P  L  H  N  T  Y  L  S  A  F

61  ATTGCGGCGTTTCCGATCGTTTTATTTCTATTATGCTTAACTGTGTTTAGGATGAGGGGA
     I  A  A  F  P  I  V  L  F  L  L  C  L  T  V  F  R  M  R  G

121  GTAAAAGCCGCTTTTCTCATTCTTTGTTTTGGTTTAGTAACAGCTGTTTTGTTTTTCCAT
     V  K  A  A  F  L  I  L  C  F  G  L  V  T  A  V  L  F  F  H

181  ATGCCGATTTCAAAGGCGATTGCTGCGTCCGTCTATGGAATCGCAAACGGTTTATGGCCG
     M  P  I  S  K  A  I  A  A  S  V  Y  G  I  A  N  G  L  W  P

241  ATTGGCTATATTGTGATTATGGCCGTCTGGCTGTATAAAATTGCTGTGAAAACGGGGAAA
     I  G  Y  I  V  I  M  A  V  W  L  Y  K  I  A  V  K  T  G  K

301  TTTGATATTATCCGCAGCAGTATTGCAAACATTTCGGAGGATCAGCGGCTTCAACTGCTG
     F  D  I  I  R  S  S  I  A  N  I  S  E  D  Q  R  L  Q  L  L

361  CTCATCGGCTTTAGCTTTAATGCTTTTTTAGAAGGAGCTGCAGGATTCGGTGTTCCGATT
     L  I  G  F  S  F  N  A  F  L  E  G  A  A  G  F  G  V  P  I

421  GCCATTTCGGCTGCTTTGCTTTCAGAACTAGGATTTCATCCATTAAAAGCGGCCGCGCTT
     A  I  S  A  A  L  L  S  E  L  G  F  H  P  L  K  A  A  A  L

481  TGCTTAATTGCCAATGCTGCCTCTGGCGCGTTTGGAGCGATAGGAATTCCGGTTATTGTC
     C  L  I  A  N  A  A  S  G  A  F  G  A  I  G  I  P  V  I  V

541  GGAGCGCAAATGGGGGATTTAACGCCGATTGAGTTATCCCGTACGCTTGCTTGGATTTTG
     G  A  Q  M  G  D  L  T  P  I  E  L  S  R  T  L  A  W  I  L

601  CCGTTTATCTCGTTTCTCATTCCATTCTTATTAGTGTTTGTCTTGGATAAGTGGAAGGGT
     P  F  I  S  F  L  I  P  F  L  L  V  F  V  L  D  K  W  K  G

661  ATTAAAGAAACATTGCCTGCTCTTTTCGTGGTAAGCGGAAGTTACACCATTGTCCAAACA
     I  K  E  T  L  P  A  L  F  V  V  S  G  S  Y  T  I  V  Q  T

721  TTGACGATCATTGTGCTTGGTCCTGAGCTGGCCAACATTTTAGCGGCGCTTGTCAGCATG
     L  T  I  I  V  L  G  P  E  L  A  N  I  L  A  A  L  V  S  M

781  GGGGCACTGGCTCTTTTCTTGAGAAAATGGCAGCCTTCAAATATATATCGAGTGAATCCG
     G  A  L  A  L  F  L  R  K  W  Q  P  S  N  I  Y  R  V  N  P

841  GATGAAAAAGGCGGAGAAAAATGCAAATACAGCTTGAAAGACATCATCAGTGCGTGGTCC
     D  E  K  G  G  E  K  C  K  Y  S  L  K  D  I  I  S  A  W  S

901  CCGTTTTATATTTTAACGGTGCTCGTTATTATATGGAGTCTGCCTGGTTTTAAAGCTCTG
     P  F  Y  I  L  T  V  L  V  I  I  W  S  L  P  G  F  K  A  L
```

```
 961 TTTGCCGAGGGAGGCGCACTGCAGCGAACGACGCTTTTGTTTAAGGTGCCATTTTTGCAT
     F   A   E   G   G   A   L   Q   R   T   T   L   L   F   K   V   P   F   L   H

1021 GGCGAAGTCGCGAAAATTCCTCCGGTGGCGCCGGCCCAGACGGCATTAGATGCCATATTT
     G   E   V   A   K   I   P   P   V   A   P   A   Q   T   A   L   D   A   I   F

1081 AAGCTAGACCTTGTATCGGCAACAGGCACGGCGATTTTACTGGCGGTGCTGTTCACAGGG
     K   L   D   L   V   S   A   T   G   T   A   I   L   L   A   V   L   F   T   G

1141 ATGTTTAGCAAAAACATTACGTTCGCGGAAGGAATACAAAGTTTAAAAGAAACATGTAAA
     M   F   S   K   N   I   T   F   A   E   G   I   Q   S   L   K   E   T   C   K

1201 GAGCTATTCATTCCTGTATTAACGATTTGTTTTATCATGGGATTTGCCAACTTAGCCGAC
     E   L   F   I   P   V   L   T   I   C   F   I   M   G   F   A   N   L   A   D

1261 TATGCAGGTTTATCCGCTGCGATTGGTTTGGCATTGGCGGAGACAGGCGATGCATTTCCA
     Y   A   G   L   S   A   A   I   G   L   A   L   A   E   T   G   D   A   F   P

1321 TTTGTTTCCCCGTTATTAGGGTGGCTTGGTGTGTTTATTACAGGATCTGTCGTGAGCAAT
     F   V   S   P   L   L   G   W   L   G   V   F   I   T   G   S   V   V   S   N

1381 AATGCTTTATTCGGCCATTTACAAGCTGTTACAGGAGCGCAAATAGGGACAAGCTCTTCG
     N   A   L   F   G   H   L   Q   A   V   T   G   A   Q   I   G   T   S   S   S

1441 TTATTGCTTGCGGCTAACACCAGCGGGGGAGTGATGGGGAAACTTATTTCCCCGCAGTCC
     L   L   L   A   A   N   T   S   G   G   V   M   G   K   L   I   S   P   Q   S

1501 ATCGCCATAGCAACTGCTGCAGTGAAAGAGACAGGCAAAGAATCTCACCTGTTTAAAATG
     I   A   I   A   T   A   A   V   K   E   T   G   K   E   S   H   L   F   K   M

1561 ACGATTTATTATAGCTTGATCCTGCTATTGTTTGTGGGAGTATGGACGTACTTTCTTTCG
     T   I   Y   Y   S   L   I   L   L   F   V   G   V   W   T   Y   F   L   S

1621 ACCGCAGGAATGTAGATCATTATGGTTTGTTATTCAGTTAGGCACCGTGTATAAATGAAA
     T   A   G   M   *   I   I   M   V   C   Y   S   V   R   H   R   V   *   M   K

1681 AAAGATGTATTTTGCGGCCTTTTC
     K   D   V   F   C   G   L   F   -
```

**The DNA Sequence of ADH from *Bacillus* LN**

Coding region underlined

```
   1  GTGGCTCCAA GCTATGTATT TTTAGCAAGC GAAGAGGCAT CCTATATTAC
  51  GGGGCAAATG ATACATGTGA ATGGCGGAAA GATTGTCAAT GGATAGAAAG
 101  CGGCGGAAAA CGGAACGTTC TTCATGACTG CGCAAATTTT ATGTAATATT
 151  TTCTGACATA GTTGTTGTGC GGTCTGTATA TCACCGTTAT GATAAAAATA
 201  CATGCTATTT CTTATCCATG TTCCTCAACC TTTTGTATGG ATTGCAAAAG
 251  GCATCCTCTC TTCCTTCACT TGCAACAATT TATTGCAAGT TTTTGTGTAT
 301  TTAGGAATAT TATATGCCGC ATCAACGGAC AGGCAATGTG AACAAAGCTG
 351  CTCCAAACAT AACATATTAT TGATATTTCT TGAAATATTA CTAATATTTT
 401  GATTAAATGT TTTTGTTTGC ACTGCAGCTT TTACAAAAGT AGAATATTTT
 451  ATGGTGTTTA TCCGAAGAAT ATCATCATGA TACCCTATGG GAGGGAATTG
 501  TGATGAAAGC TGCAGTAGTA GAGCAATTTA AGGAACCATT AAAAATTAAA
 551  GAAGTGGAAA AGCCATCCAT TCATATGGC GAAGTATTAG TCCGCATTAA
 601  AGCATGCGGT GTATGCCATA CGGACTTGCA TGCCGCTCAC GGCGATTGGC
 651  CAGTAAAACC AAAACTTCCT TTAATCCCTG GCCATGAAGG AGTCGGAATT
 701  GTTGAAGAAG TCGGTCCGGG GGTAACCCAT TTAAAAGTGG GAGACCGCGT
 751  TGGAATTCCT TGGTTATATT CTGCTTGCGG CCATTGCGAA TATTGTTTAA
 801  GCGGACAAGA GACATTATGT GAACATCAAG AAAACGCCGG CTACTCAGTC
 851  GACGGGGGGT ATGCAGAATA TTGCAGAGCT GCGGCAGACT ATGTGGTGAA
 901  AATTCCTGAC AACTTGTCGT TTGAAGAAGC TGCTCCTATT TTCTGCGCCG
 951  GAGTTACTAC TTATAAAGCG TTAAAAGTCA CAGGTACAAA ACCGGGAGAA
1001  TGGGTAGCGA TCTATGGCAT CGGTGGCCTT GGACATGTTG CCGTCCAGTA
1051  TGCGAAAGCG ATGGGGCTTC ATGTTGTTGC AGTGGATATC GGCGATGAGA
```

```
1101  AACTGGAACT TGCAAAAGAG CTTGGCGCCG ATCTTGTTGT AAATCCTGCA

1151  AAAGAAAATG CGGCACAATT TATGAAAGAG AAAGTCGGCG GAGTACACGC

1201  GGCTGTTGTG ACAGCTGTAT CTAAACCTGC TTTTCAATCT GCGTACAATT

1251  CTGTCCGCAG AGGCGGCACG TGCGTGCTTG TCGGATTACC GCCGGAAGAA

1301  ATGCCTATTC CAATCTTTGA TACGGTATTA ACGGAATTA AAATTATCGG

1351  TTCCATTGTC GGCACGCGGA AAGACTTGCA AGAAGCGCTT CAGTTCGCTG

1401  CAGAAGGTAA AGTAAAAACC ATTATTGAAG TGCAACCTCT TGAAAAAATT

1451  AACGAAGTAT TTGACAGAAT GCTAAAAGGA GAAATTAACG GACGGGTTGT

1501  TTTAACGTTA GAAAATAATA ATTAACGTCA ACAACACAAT GTTGACAACC

1551  CGGCATTCTA GGGCTGTCTC ATC
```

*Fig. 8 (contd)*

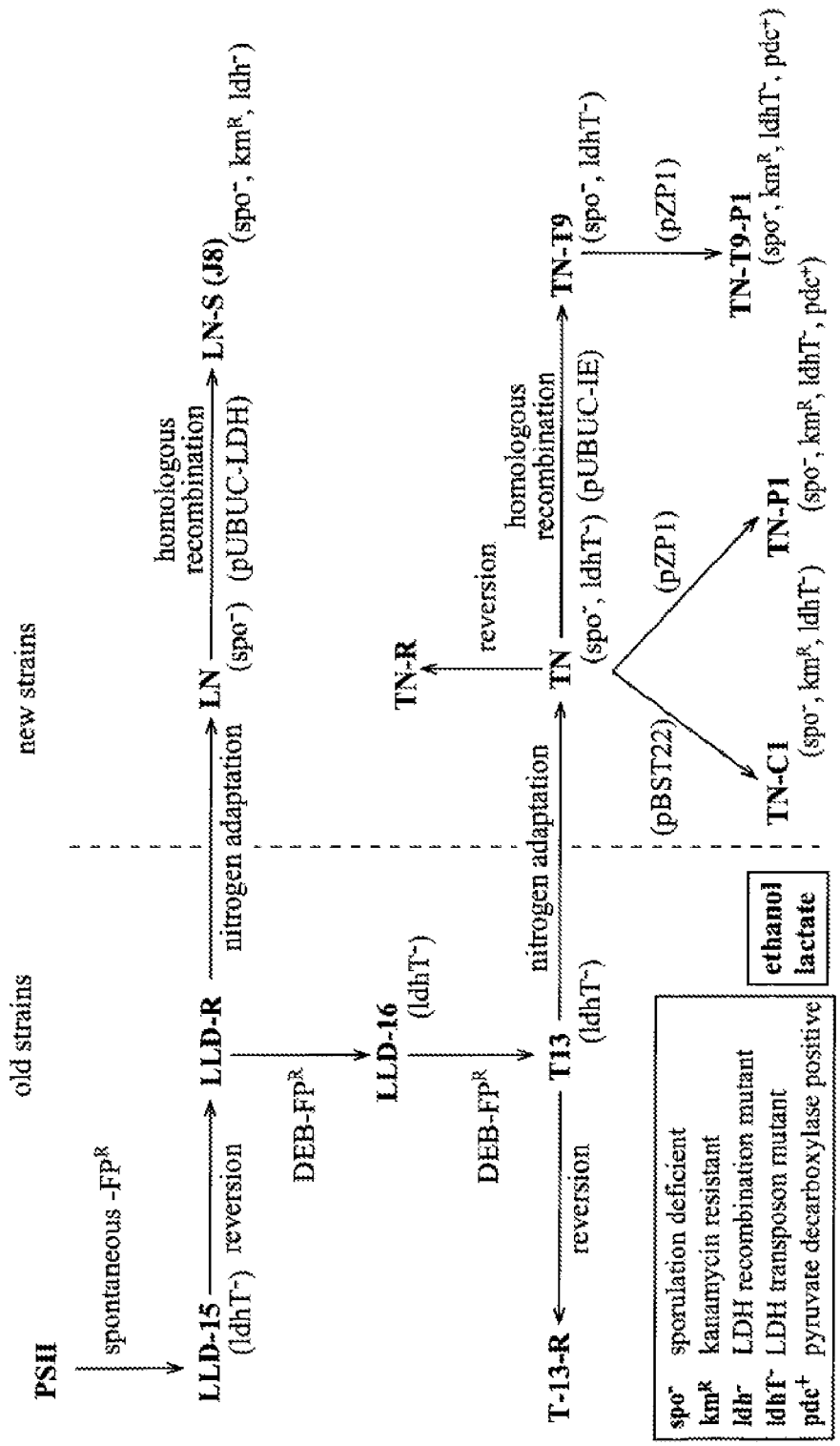
Fig. 9A Strain Development

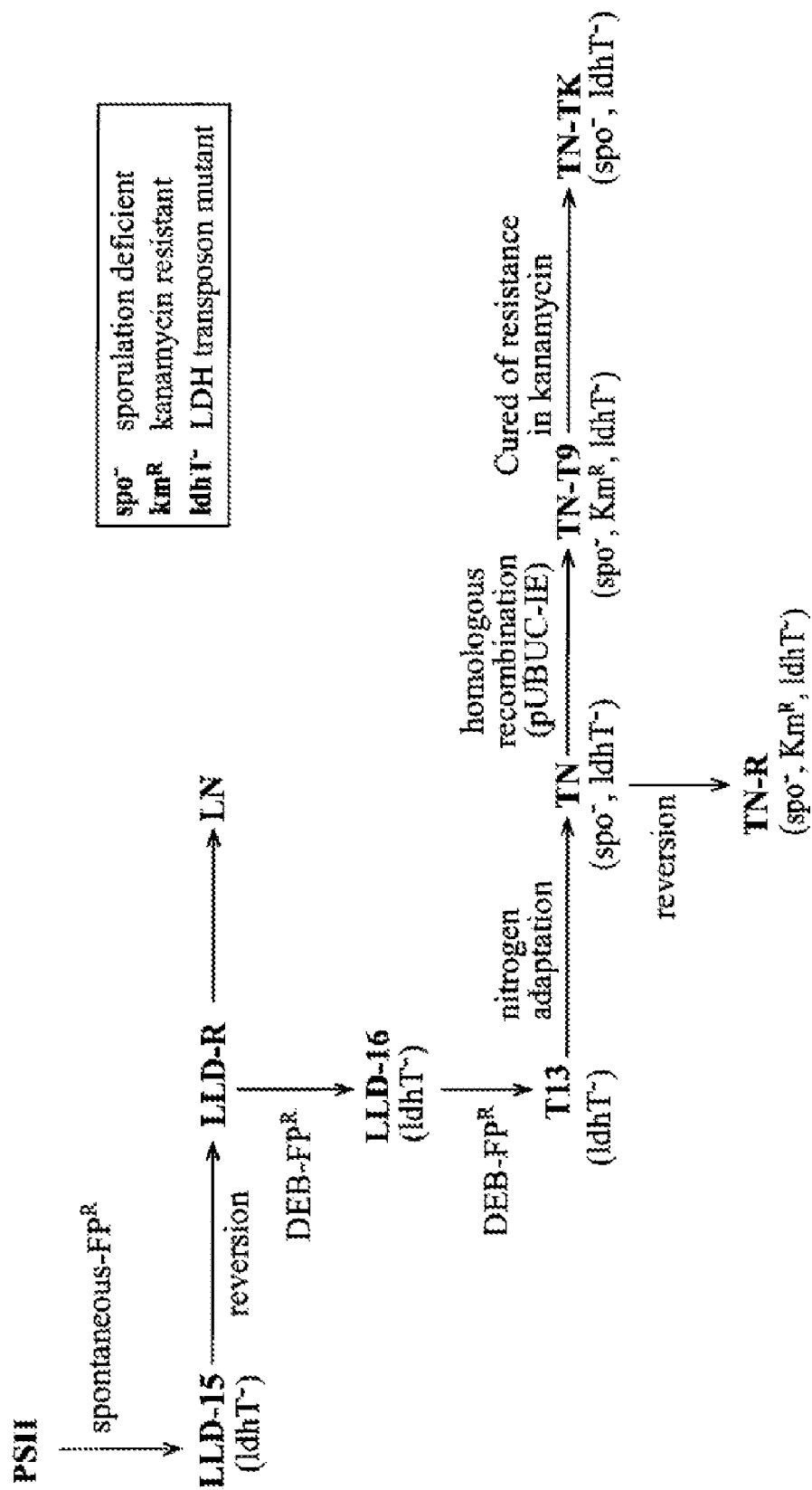
Fig. 9B Development of Bacillus strains TN-T9 and TN-TK

Construction of an Artificial PDC operon

ETHANOL PRODUCTION IN *BACILLUS*

This application is a continuation of Ser. No. 11/108,870 filed Apr. 19, 2005, now abandoned, which is a continuation of Ser. No. 09/971,361 filed Oct. 5, 2001, now abandoned, which claims the benefit of Ser. No. 60/247,017 filed Nov. 13, 2000, and GB 0024554.8, filed Oct. 6, 2000, now expired. Each of these applications is incorporated herein by reference in its entirety.

This application incorporates by reference the contents of a 37.4 kb text file created on Feb. 13, 2009 and named "sequence_listing.txt," which is the sequence listing for this application.

This invention relates to the production of ethanol as a product of bacterial fermentation. In particular this invention relates to a novel method of gene inactivation and gene expression based upon homologous recombination.

Many bacteria have the natural ability to metabolise simple sugars into a mixture of acidic and neutral fermentation products via the process of glycolysis. Glycolysis is the series of enzymatic steps whereby the six carbon glucose molecule is broken down, via multiple intermediates, into two molecules of the three carbon compound pyruvate. The glycolytic pathways of many bacteria produce pyruvate as a common intermediate. Subsequent metabolism of pyruvate results in a net production of NADH and ATP as well as waste products commonly known as fermentation products. Under aerobic conditions, approximately 95% of the pyruvate produced from glycolysis is consumed in a number of short metabolic pathways which act to regenerate NAD.sup.+ via oxidative metabolism, where NADH is typically oxidised by donating hydrogen equivalents via a series of steps to oxygen, thereby forming water, an obligate requirement for continued glycolysis and ATP production.

Under anaerobic conditions, most ATP is generated via glycolysis. Additional ATP can also be regenerated during the production of organic acids such as acetate. NAD.sup.+ is regenerated from NADH during the reduction of organic substrates such as pyruvate or acetyl CoA. Therefore, the fermentation products of glycolysis and pyruvate metabolism include organic acids, such as lactate, formate and acetate as well as neutral products such as ethanol.

The majority of facultatively anaerobic bacteria do not produce high yields of ethanol either under aerobic or anaerobic conditions. Most facultative anaerobes metabolise pyruvate aerobically via pyruvate dehydrogenase (PDH) and the tricarboxylic acid cycle (TCA).

Under anaerobic conditions, the main energy pathway for the metabolism of pyruvate is via the pyruvate-formate-lyase (PFL) pathway to give formate and acetyl-CoA. Acetyl-CoA is then converted to acetate, via phosphotransacetylase (PTA) and acetate kinase (AK) with the co-production of ATP, or reduced to ethanol via acetaldehyde dehydrogenase (AcDH) and alcohol dehydrogenase (ADH). In order to maintain a balance of reducing equivalents, excess NADH produced from glycolysis is re-oxidised to $NAD^+$ by lactate dehydrogenase (LDH) during the reduction of pyruvate to lactate. NADH can also be re-oxidised by AcDH and ADH during the reduction of acetyl-CoA to ethanol but this is a minor reaction in cells with a functional LDH. Theoretical yields of ethanol are therefore not achieved since most acetyl CoA is converted to acetate to regenerate ATP and excess NADH produced during glycolysis is oxidised by LDH.

Ethanologenic microorganisms, such as *Zymomonas mobilis* and yeast, are capable of a second type of anaerobic fermentation commonly referred to as alcoholic fermentation in which pyruvate is metabolised to acetaldehyde and $CO_2$ by pyruvate decarboxylase (PDC). Acetaldehyde is then reduced to ethanol by ADH regenerating $NAD^+$. Alcoholic fermentation results in the metabolism of 1 molecule of glucose to two molecules of ethanol and two molecules of $CO_2$. DNA which encodes both of these enzymes in *Z. mobilis* has been isolated, cloned and expressed recombinantly in hosts capable of producing high yields of ethanol via the synthetic route described above. For example; US 5,000,000 and Ingram et al (1997) *Biotechnology and Bioengineering* 58, Nos. 2 and 3 have shown that the genes encoding both PDC (pdc) and ADH (adh) from *Z. mobilis* can be incorporated into a "pet" operon which can be used to transform *Escherichia coli* strains resulting in the production of recombinant *E. coli* capable of co-expressing the *Z. mobilis* pdc and adh. This results in the production of a synthetic pathway re-directing *E. coli* central metabolism from pyruvate to ethanol during growth under both aerobic and anaerobic conditions. Similarly, U.S. Pat. No. 5,554,520 discloses that pdc and adh from *Z. mobilis* can both be integrated via the use of a pet operon to produce Gram negative recombinant hosts, including *Erwina*, *Klebsiella* and *Xanthomonas* species, each of which expresses the heterologous genes of *Z. mobilis* resulting in high yield production of ethanol via a synthetic pathway from pyruvate to ethanol.

U.S. Pat. No. 5,482,846 discloses the simultaneous transformation of mesophilic Gram positive *Bacillus* sp with heterologous genes which encode both the PDC and ADH enzymes so that the transformed bacteria produce ethanol as a primary fermentation product. There is no suggestion that bacteria transformed with the pdc gene alone will produce ethanol.

EP-A-0761815 describes a method of homologous recombination whereby a sporulation gene is inserted into *Bacillus thurengiensis*.

EP-A-0603416 describes a method of homologous recombination whereby an arbitrary gene is inserted into *Lactobacillus delbrueckii*.

EP-A-0415297 describes a method of producing *Bacillus* strains expressing a mutant protease.

Biwas et al., (J. Bacteriol., 175, 3628-3635, 1993) describes a method of homologous recombination whereby *Lactococcus lactis* has a chromosomal gene replaced by a plasmid carried modified copy. The method uses a thermosensitive plasmid and cannot be used to transform a thermophilic bacterium.

A key improvement in the production of ethanol using biocatalysts can be achieved with thermophilic microorganisms that operate at high temperature. The conversion rate of carbohydrates into ethanol is much faster. For example, ethanol productivity in a thermophilic *Bacillus* is up to ten-fold faster than a conventional yeast fermentation process which operates at 30° C. Consequently, a smaller production plant is required for a given volumetric productivity, thereby reducing plant construction costs. At high temperature, there is a reduced risk of contamination in the fermenter from other microorganisms, resulting in less downtime, increased plant productivity and a lower energy requirement for feedstock sterilisation. Moreover, fermentation cooling is not required, reducing operating costs further. The heat of fermentation helps to evaporate ethanol, which reduces the likelihood of growth inhibition from high ethanol concentrations, a common problem with most bacterial fermentations. Ethanol evaporation in the fermenter head space also facilitates product recovery.

The inventors' strain originates from a wild-type isolate that is a natural composting organism and far more suited for the conversion of sugars found in agricultural feedstocks to ethanol than traditional mesophilic microorganisms. The base strain possesses all the genetic machinery for the conversion of hexose and pentose sugars, and cellobiose to ethanol; the inventors have simply blocked the LDH pathway to increase ethanol yields. This process is called self-cloning and does not involve expression of foreign DNA. Consequently, the resulting organism does not fall under the safety regulations imposed on the use of genetically modified organisms (GMOs).

In contrast, conventional biocatalysts are either good ethanol producers unable to utilise pentose sugars or poor ethanol producers that can utilise pentose sugars. These organisms have been genetically modified using complex genetic techniques so that they can convert both hexose and pentose sugars to ethanol. However, there are doubts about the stability of these recombinant organisms and concerns over safety since such organisms fall under the GMO safety regulations. Moreover, recombinant mesophiles have expensive nutrient requirements and are sensitive to high salt concentrations and feedstock inhibitors.

The metabolic reactions leading to lactic acid formation (LDH pathway) have been blocked by chemical mutagenesis and the resulting strain TN is lactate negative and produces ethanol in high yield. However, the mutant strain is unstable and spontaneously reverts to the lactate-producing wild-type. Revertants grow faster than the mutant at low pH and in high sugar concentrations, and rapidly 'take-over' in continuous culture. During 'take-over', the main fermentation product changes from ethanol to lactate.

The inventors initiated a molecular biology program to tackle the stability problem and gain a better insight into the genetic systems involved in ethanol formation. The inventors first developed genetic techniques to specifically manipulate the organism and a sporulation deficient mutant amenable to genetic manipulation was then selected in continuous culture. The inventors then sequenced several key metabolic genes; lactate dehydrogenase (ldh), lactase permease (lp), alcohol dehydrogenase (adh) and a novel insertion sequence located within the ldh gene. DNA sequence analysis of the ldh gene from the chemically mutated strain revealed that the gene had been inactivated by the insertion of a naturally occurring insertion sequence element (IE) (also referred to as an IS element) in the coding region of the gene. Transposition into (and out of) the ldh gene and subsequent gene inactivation is itself unstable, resulting in reversion.

The inventors determined that the IE sequence within the ldh gene provides a large area for homologous recombination. It was therefore proposed that the stability of the ldh mutation could be improved by integration of plasmid DNA into the IE sequence already present within the ldh gene of strain TN.

The stability of the ldh gene mutation was improved by specific homologous recombination between a plasmid and the insertion sequence within the ldh gene. The resulting strain is a sporulation deficient, facultatively anaerobic, Gram-positive *Bacillus* which exhibits improved ethanol production characteristics in continuous culture. Results show that this new type of mutant is completely stable and has superior growth characteristics and ethanol productivity than the first mutants generated by chemical mutagenesis.

Strain improvement has been achieved through a novel method of gene integration based on homologous recombination. The site of integration and plasmid for recombination can also be used to integrate and overexpress native or heterologous genes.

Southern hybridisation studies indicated that 3 copies of a transposable insertion sequence element (E) are present on the chromosome of *Bacillus* strain LLD-R. The insertion sequence is 3.2 kb long and comprises three DNA open reading frame sequences (ORF's) that are potentially translatable into proteins. ORF1 exhibits no homology to any protein in the National Center for Biotechnology Information (NCBI) database whereas istA and istB display significant homology to a family of known transposase enzymes. *Bacillus* strain TN was developed from LLD-R following chemical mutagenesis (FIGS. 9A and 9B), and one copy of the insertion sequence was found within the structural ldh gene resulting in inactivation of the ldh gene and a lactate negative phenotype, the main metabolic product of fermentation thereby changing from lactate to ethanol. The DNA sequence of the ldh gene (SEQ ID NO:1) and the IE sequence (underlined; SEQ ID NO:16) from *Bacillus* strain TN are shown in FIG. 1. The amino acid sequence of L-LDH is shown in SEQ ID NO:9.

However, this insertion proved to be relatively unstable and the mutant strain TN spontaneously reverts back to strain TN-R with a functional ldh gene. The main metabolic product of fermentation changes from ethanol to lactate as shown in FIG. 2 which shows the genetic instability of *Bacillus* mutant strain TN.

The IE sequence was amplified from TN chromosomal DNA by PCR. Primers were chosen from the ldh gene sequence that flanked the insertion sequence and a HindIII restriction site was introduced into the upstream primer and a XbaI restriction site was introduced into the downstream primer to create convenient restriction sites for subsequent cloning into plasmid pUBUC. A 3.2 kb PCR fragment containing the insertion sequence was trimmed using HindIII and XbaI restriction endonucleases and subsequently cloned into plasmid pUBUC resulting in plasmid pUBUC-IE (FIG. 5).

In vivo methylation of plasmid DNA to prevent its restriction after transformation of *Bacillus* sp. was achieved after transformation, propagation in and purification from *E. coli* TOP 10 cells harbouring plasmid pMETH. Methylated pUBUC-IE was then used to transform *Bacillus* strain TN. Transformants were first isolated on TGP agar plates (kanamycin) at 52° C. Transformants were then screened using PCR amplification of the ldh gene. Failure to amplify a PCR product (greater than 10 kb using set PCR conditions) using LDH primers suggested that at least one copy of the plasmid had become integrated into the chromosome.

The new strain, TN-T9, was grown under pH controlled conditions in continuous culture without kanamycin selection to check for strain stability. Stability of strain TN-T9 was confirmed using sub-optimal fermentation conditions such that residual sugar was present within the fermentation medium; conditions which favour reversion. The fermentation ran continuously for 750 hours without any trace of lactate production despite the presence of residual sugar within the fermentation medium, pyruvate excretion and numerous deviations from the set conditions. Ethanol was produced in relatively large amounts throughout the fermentation FIG. 4, indicating that the ldh gene mutation in strain TN-T9 is stable in continuous culture under the experimental conditions provided.

The inventors have also optimised the fermentation conditions for cell growth and ethanol production for *Bacillus* strain TN-T9.

In summary the inventors have developed a dual system for improving the stability of the ldh mutant whilst expressing pdc and adh genes optionally using a pdc/adh operon. The inventors have also isolated and sequenced a novel ldh gene and insertion sequence element, as well as novel lactate permease and alcohol dehydrogenase genes. Furthermore, the inventors have developed a technique for the integration of plasmid DNA into the chromosome and selection of recombinant *Bacillus* sp and have developed a set of optimised conditions for the production of ethanol by bacterial fermentation.

Accordingly, a first aspect of the present invention relates to a recombinant thermophilic, Gram-positive bacterium which has been transformed using a method of homologous recombination for stabilising a gene mutation and for inserting an expressible gene.

The invention also provides a recombinant thermophilic, Gram-positive bacterium in which the stability of the ldh mutation has been enhanced by homologous recombination between a plasmid and the chromosomal DNA of the bacterium resulting in a strain for the production of ethanol as a product of bacterial fermentation.

Preferably, the Gram-positive bacterium is a strain of *B. thermoglucosidasius*.

Preferably, the Gram-positive bacterium has been transformed with a plasmid harbouring an IE sequence as set forth in FIG. 1 (SEQ ID NO:16), or a functional portion or variant thereof. Advantageously, the IE sequence of FIG. 1 (SEQ ID NO:16), or functional variant or portion thereof, is stably incorporated into the chromosome of the recombinant bacterium by homologous recombination.

Preferably, integration of the IE sequence into the chromosome of the recombinant bacterium will result in the inactivation of the native ldh gene.

Preferably, the Gram-positive bacterium is *Bacillus* strain TN-T9 (NCIMB Accession no. NCIMB 41075 deposited on 8 Sep. 2000 in accordance with the terms of the Budapest Treaty).

Alternatively, it is preferred that the Gram-positive bacterium is *Bacillus* strain TN-TIC (NCIMB Accession no. NCIMB 41115 deposited on 27 Sep. 2001 in accordance with the terms of the Budapest Treaty).

The present invention also relates to a Gram-positive bacterium obtained by selecting mutants of TN-T9 which are kanamycin sensitive. A suitable method for obtaining such strains is described in the appended examples.

Preferably, the Gram-positive bacterium is sporulation deficient.

According to a second aspect of the present invention there is provided a Gram-positive bacterium wherein a native ldh gene has been inactivated by homologous recombination and one or more expressible genes have been inserted into the chromosomal DNA of the bacterium. Furthermore, gene expression may be increased by increased gene copy number following multiple insertions of the plasmid into the insertion sequence either as a result of one round or repeated rounds of integration.

The one or more expressible genes may be inserted into one or more IE sequences present in the chromosomal DNA of the bacterium. For example, there are 3 IE sequences on the chromosome of strains TN-T9 and TN-TK.

The gene to be expressed may be native to *Bacillus* such as alcohol dehydrogenase or foreign (i.e. heterologous such as pyruvate decarboxylase from *Z. mobilis* and α-amylase from *B. stearothermophilus*. The genes may also be arranged in an operon under the same transcriptional control. Gene expression may be regulated by manipulating the copy number of the gene and by using different transcriptional promoter sequences.

Preferably, the one or more genes are pdc and/or adh.

The amino acid sequence of adh is shown in SEQ ID NO:10.

According to a third aspect of the invention there is provided a method of inactivating a native ldh gene and inserting one or more expressible genes into the chromosome of a bacterium by homologous recombination.

Preferably the bacterium is a thermophilic Gram-positive bacterium.

Preferably, the gene to be inactivated is a native ldh gene and the one or more expressible genes are a pdc gene and a adh gene.

Preferably, the pdc gene and the adh gene form part of a PDC operon operatively linked to the IE sequence of FIG. 1 (SEQ ID NO:16) on the same plasmid.

Preferably the pdc gene is heterologous to the cell.

Preferably, both the IE sequence of FIG. 1 (SEQ ID NO:16) and the PDC operon, or portions thereof, are stably integrated into the chromosome of the bacterium.

Advantageously, the method of gene inactivation and expression comprises the use of a shuttle vector, as set forth in FIG. 5, which is able to replicate in *E. coli* and *Bacillus* strains at temperatures up to 54° C.

According to a fourth aspect of the present invention there is provided a shuttle vector which is able to replicate in both *E. coli* and *Bacillus* sp at temperatures up to 54° C., which confers resistance to ampicillin and kanamycin and which harbours the IE sequence, or a portion thereof as set forth in FIG. 1 (SEQ ID NO:16), from *Bacillus* strain TN.

Preferably, the shuttle vector is pUBUC-IE as set forth in FIG. 5.

Preferably, the shuttle vector will contain a PDC operon comprising a pdc gene and a adh gene under the control of the ldh promoter and operably linked to the IE sequence of FIG. 1 (SEQ ID NO:16).

According to a fifth aspect of the present invention there is provided a method of selecting for recombinant *Bacillus* sp at high temperature wherein plasmid DNA has been stably integrated into the ldh gene of the recombinant bacterium by homologous recombination, comprising use of PCR to select for recombinants that do not contain the native ldh gene and E sequence.

Preferably, successful integration of the insertion sequence into the ldh gene will be indicated by failure to amplify a PCR product from the ldh gene of the recombinant bacterium.

The present invention also provides one or more polypeptides encoded by the sequence shown in FIG. 1 from nucleotide 652 to nucleotide 3800, or a functional variant or portion thereof wherein the one or more polypeptides have the biological activity of a transposase.

The one or more polypeptides may have the biological activity of a transposase taken alone or when combined with other polypeptides.

Preferably, the one or more polypeptides has the amino acid sequence shown in SEQ ID NO:11, 12, or 13 or a functional portion or variant thereof.

The functional portions or variants retain at least part of the transposase function of the polypeptide shown in SEQ ID NO:11, 12, or 13. Preferably the portions are at least 20, more preferably at least 50 amino acids in length. Furthermore, it is preferred that the variants have at least 80%, more preferably at least 90% and most preferably at least 95% sequence homology with the polypeptide shown in SEQ ID NO:11, 12, or 13. Homology is preferably measured using the BLAST program.

According to a sixth aspect of the invention there is provided a DNA sequence as set forth in FIG. 6 (SEQ ID NO:2), or a functional variant thereof, which codes for a polypeptide having the biological activity of the enzyme lactate dehydrogenase.

According to a seventh aspect of the present invention there is provided a DNA sequence as set forth in FIG. 7B (SEQ ID NO:6), or a functional variant thereof, which codes for a polypeptide having the biological activity of the enzyme lactate permease.

According to an eighth aspect of the present invention there is provided a DNA sequence as set forth in FIG. 8 (SEQ ID NO:8), or a functional variant thereof, which codes for a polypeptide having the biological activity of the enzyme alcohol dehydrogenase.

In this specification, functional variants include DNA sequences which as a result of sequence additions, deletions or substitutions, or which by virtue of the degeneracy of the genetic code, hybridise to and/or encode a polypeptide having a lactate dehydrogenase lactate permease or alcohol deydrongenase activity. Preferably, the variants have at least 80%, more preferably 90% and most preferably 95% sequence homology to the sequence shown in the Figures. Homology is preferably measured using the BLAST program.

A ninth aspect of the invention also provides a method for improving the stability of the ldh mutant comprising expressing genes using a pdc/adh operon.

A tenth aspect of the present invention relates to a technique for the integration and selection of recombinant *Bacillus* sp in accordance with the invention.

According to the final eleventh aspect of the present invention there is provided a process for the production of ethanol by bacterial fermentation of the Gram-positive bacterium of the present invention comprising optimised fermentation conditions of pH, temperature, redox values and specific dilution rates for cell growth and ethanol production. Preferably, the fermentation conditions will comprise a pH range of between 5.5-7.5 and a temperature range of 40-75° C. with redox values being between −360-400 mV and dilution rates between 0.3 and 0.8 $h^{-1}$.

BRIEF DESCRIPTION OF THE DRAWINGS

The production of recombinant bacteria in accordance with the present invention will now be described, by way of example only, with reference to the drawings in which:

FIG. 1 shows the nucleotide sequence of a DNA sequence (SEQ ID NO:1) comprising an insertion element (IE), wherein the IE sequence is underlined (SEQ ID NO:16).

FIG. 2 is a schematic representation of the genetic instability of strain TN.

FIG. 6 shows the DNA sequence of a novel lactate dehydrogenase gene (SEQ ID NO:2) and translated amino acid sequence (SEQ ID NO:3) from *Bacillus* strain LN.

FIG. 7A shows the partial DNA sequence of a novel lactate permease gene (SEQ ID NO:4) and the translated amino acid sequence (SEQ ID NO:5) from *Bacillus* strain LN.

FIG. 7B shows the full DNA sequence of a novel lactate permease gene (SEQ ID NO:6) and the translated amino acid sequence (SEQ ID NO:7) from *Bacillus* strain LN.

FIG. 8 shows the DNA sequence (SEQ ID NO:8) of a novel alcohol dehydrogenase gene (underlined) from *Bacillus* strain LN.

FIG. 9A is a schematic representation showing the development of *Bacillus* strain TN-T9. FIG. 9B is a schematic representation showing the development of *Bacillus* strains TN-T9 and TN-TK.

EXAMPLES

Materials and Methods
Construction of Plasmid pUBUC

A shuttle vector for the transfer of DNA between *E. coli* and the inventor's thermophilic *Bacillus* strains was developed by fusing plasmids pUC 18 and pUB 110. Plasmid pUB 110 is a widely used vector that was isolated from *Staphylococcus aureus* which confers resistance to kanamycin and which can replicate in *B. stearothermophilus* at temperatures up to 54° C. Narumi et al., 1992 Biotechnology Techniques 6, No. 1. Plasmids pUB 110 and pUC18 were linearised with EcoR1 and BamH1, and then ligated together to form pUBUC (6.4 kb). Plasmid pUBUC has a temperature sensitive replicon, and cannot replicate above 54° C. making it an ideal host for gene integration, via homologous recombination at elevated temperatures.

Construction of Plasmid pMETH

A 1.1 kb fragment containing the met gene was amplified from *Haemophilus aeygptius* chromosomal DNA by PCR. The gene was verified by DNA sequencing. The met gene was trimmed with BamHI and XbaI, and then subcloned into the expression plasmid pCL1920, previously linearised with BamH1 and XbaI. The resultant plasmid pMETH was transformed into *E. coli* TOP 10. *E. coli* TOP 10 cells harbouring pMETH were propagated and the culture was harvested for subsequent transformation and in vivo methylation using a method described by Tang et al (1994) Nuc. Acid Res. 22 (14). Competent cells were stored in convenient aliquots at −70° C. prior to transformation.

PCR Amplification

The IE sequence was amplified from TN chromosomal DNA by PCR using primers LDH7 and LDH8. The concentration of reactants and the PCR procedure used were those recommended in the Expand™ High Fidelity PCR System (Roche Diagnostics). PCR amplification from lyophilised cells was achieved after 30 cycles in a Genius thermocycler (Techne, Ltd., Cambridge). The sequence of the upstream primer, LDH7, was 5'-AAGCTT GAT GAA ATC CGG ATT TGA TGG-3' (SEQ ID NO:14) and the sequence of the downstream primer, LDH8 was 5'-TCTAGA GCT AAA TTT CCA AGT AGC-3' (SEQ ID NO:15). These primers were chosen from the ldh gene sequence that flanked the insertion sequence. A HindIII restriction site was introduced into the upstream primer and a XbaI restriction site was introduced into the downstream primer to create convenient restriction sites for subsequent cloning (introduced sites are underlined).

Construction of Plasmid pUBUC-IE

Figure 3:
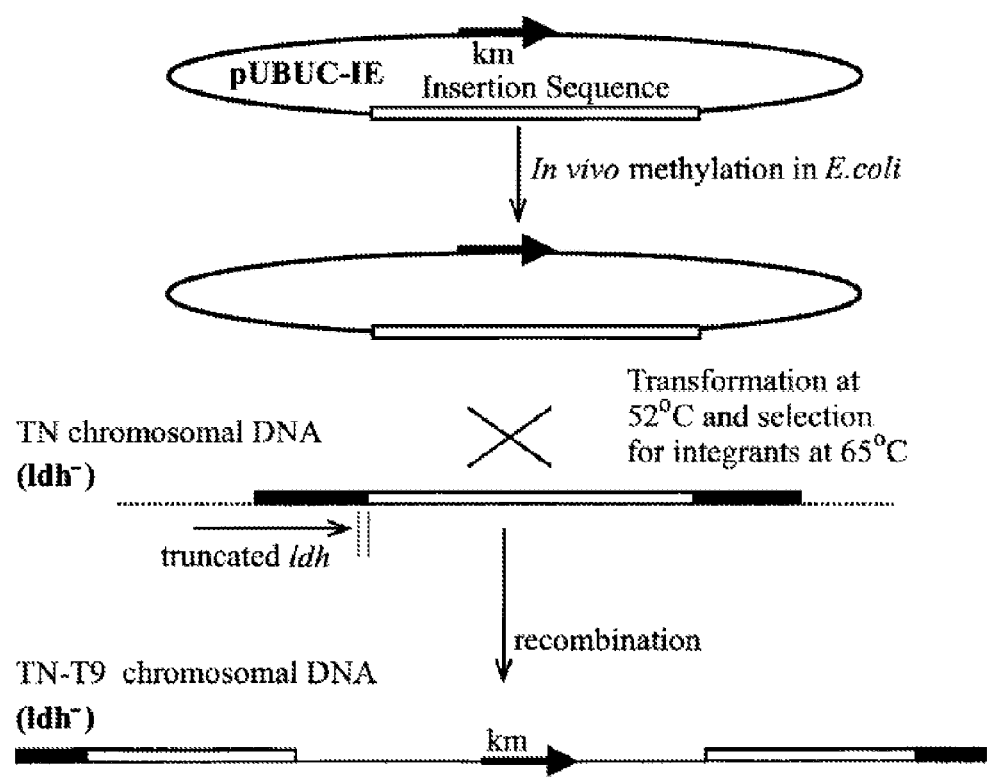
FIG. 3 is a schematic representation of the method for LDH gene inactivation by single-crossover recombination in *Bacillus* mutant strain TN.
Figure 4:
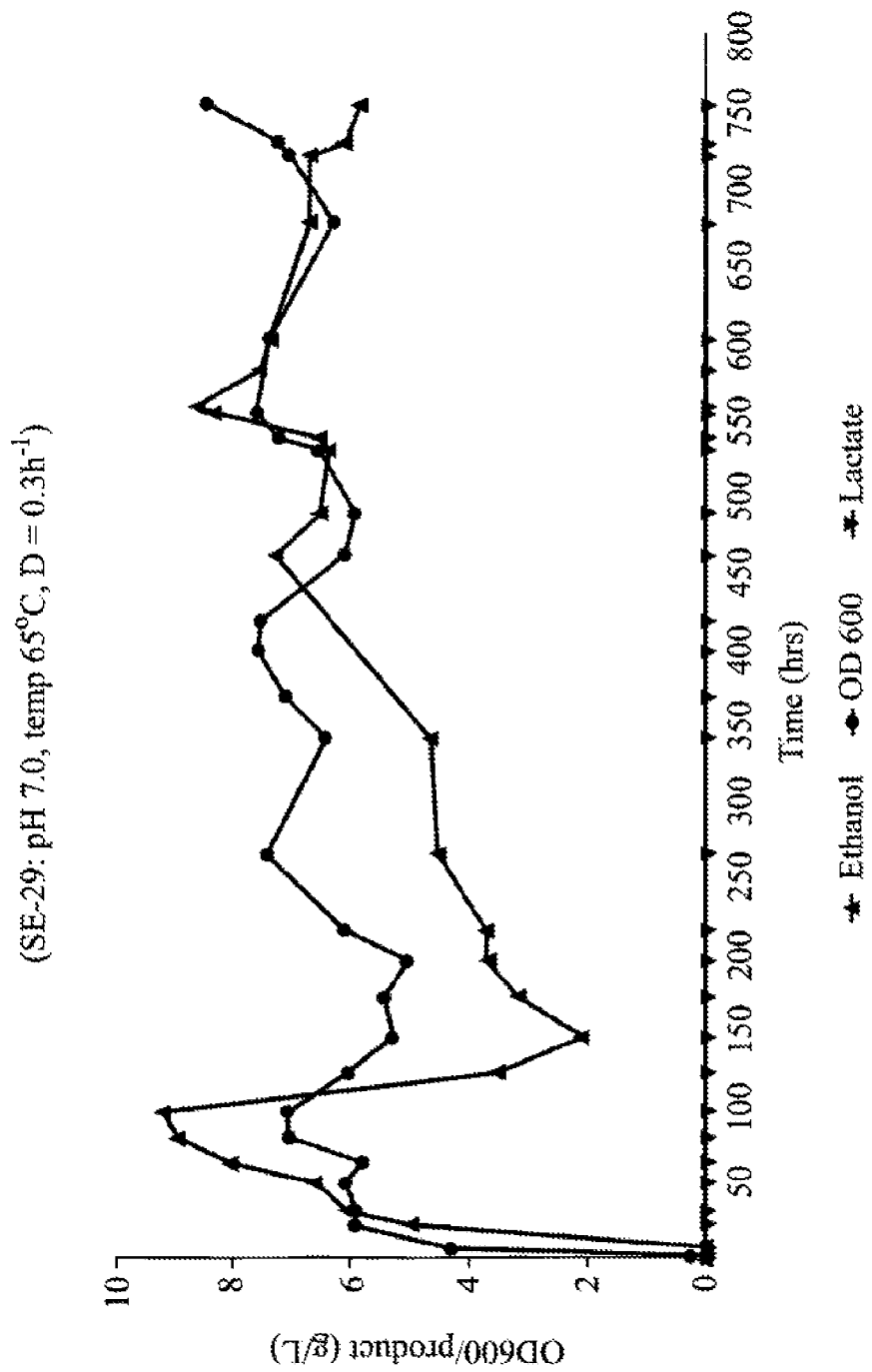
FIG. 4 is a graphical representation showing the stability of *Bacillus* mutant strain TN-T9 in continuous culture for over 750 hours.
Figure 5:
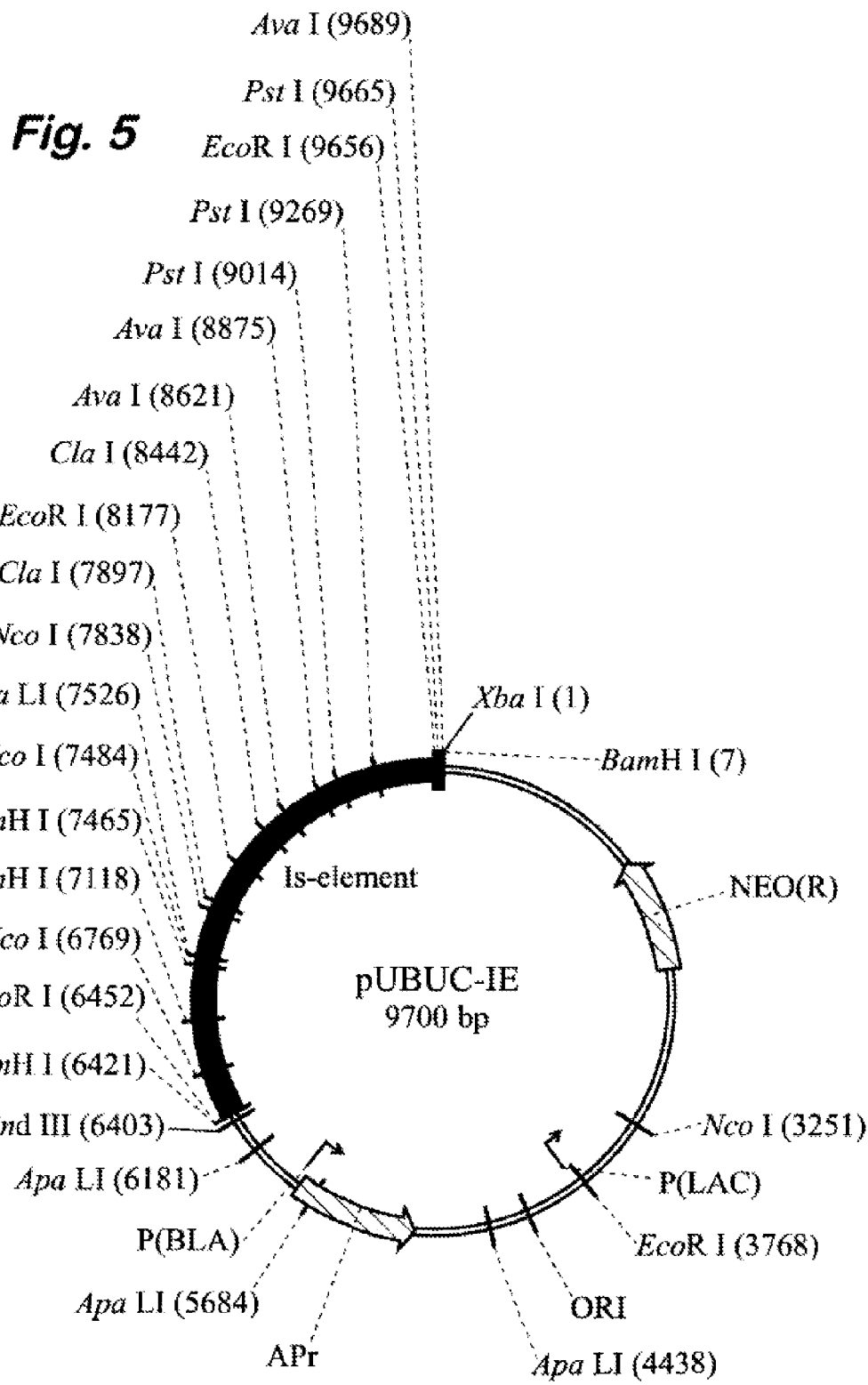
FIG. 5 is a schematic representation of shuttle vector pUBUC-IF.
Figure 10:
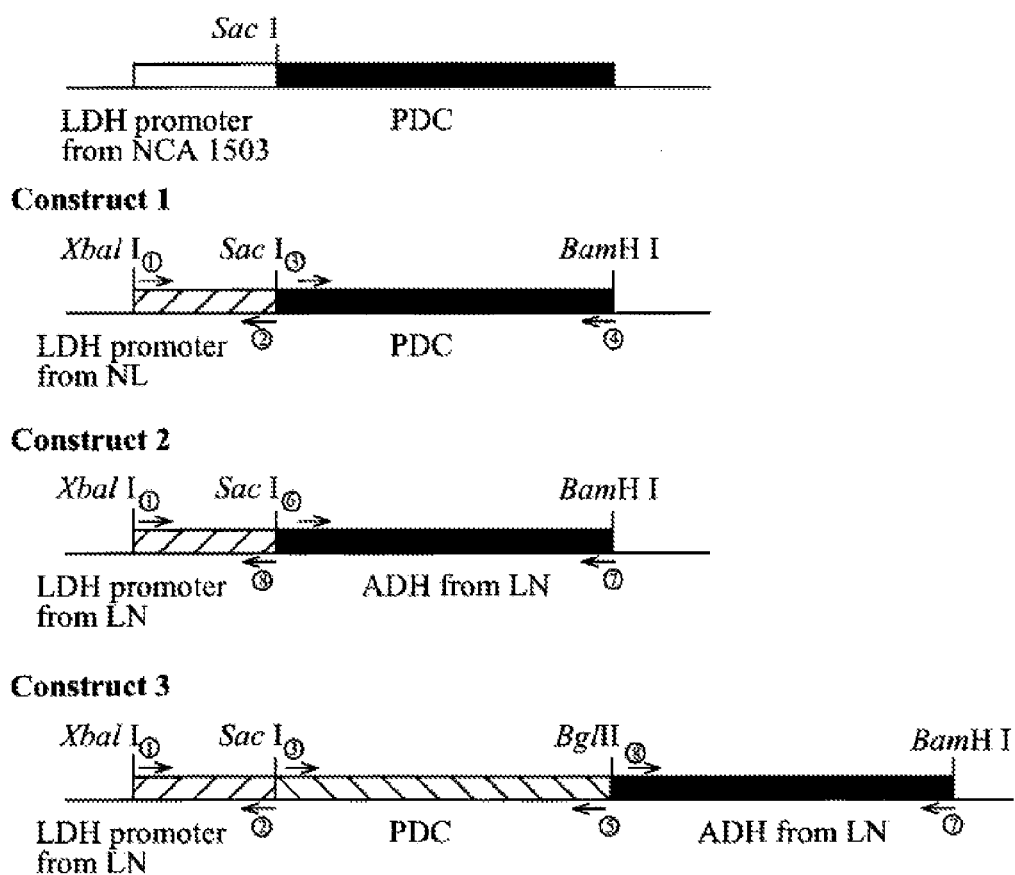
FIG. 10 shows the construction of an artificial PDC operon.

The manipulation, transformation and isolation of plasmid DNA in *E. coli* was performed using standard procedures (Maniatis). A 3.2 kb PCR fragment containing the insertion sequence was trimmed with HindIII and XbaI and then cloned into plasmid pUBUC. The resulting shuttle plasmid, referred to as pUBUC-IE (FIG. 5) can replicate in *E. coli* and *Bacillus* strains at temperatures up to 54° C., confers resistance to ampicillin and kanamycin, and harbours the IE sequence from *Bacillus* strain TN.

Construction of PDC Operon

*Bacillus* strain TN converts the intracellular metabolite pyruvate to acetyl-CoA via the PFL or PDH pathway. Acetyl-CoA is then reduced to acetaldehyde and then to ethanol in reactions catalysed by AcDH and ADH, respectively. The introduction of a foreign PDC enzyme provides the cells with an alternative pathway for ethanol production that involves decarboxylation of pyruvate by PDC to form acetaldehyde which is then reduced to ethanol by the native ADH enzyme. Both PDC and ADH are involved in the conversion of pyruvate to ethanol.

We have shown that expression of *Z. mobilis* pdc from plasmid pZP-1 improves cell growth and stability of the mutant strain TN. However, we did not see any significant increase in ethanol formation. Therefore, we decided to increase pdc gene expression and co-express the native adh gene from *Bacillus* TN.

In plasmid pZP-1, the pdc gene was placed under the control of the ldh promoter sequence from *B. stearothermophilus* NCA1503. We decided to change the promoter with the ldh promoter from *Bacillus* LN (construct 1). We then placed the adh gene from *Bacillus* strain LN under the control of the ldh promoter (construct 2). Finally, both pdc (from *Z. mobilis* and adh (from *Bacillus* LN) were placed under the control of the ldh promoter sequence (construct 3). All the genes have been amplified by PCR from *Z. mobilis* (pdc) and *Bacillus* strain LN (ldh promoter and pdc), trimmed with the appropriate restriction enzymes, ligated together and cloned into an *E. coli* plasmid vector. The 3 constructs were cloned into the replicative shuttle vectors pUBUC, pFC1 or the integrative shuttle vector pUBUC-IE for chromosomal integration.

Example 1

Transformation of TN

Plasmid pUBUC-IE was methylated in vivo after transformation, propagation in and purification from *E. coli* TOP10 cells harbouring plasmid pMETH. Methylated pUBUC-IE was then used to transform *Bacillus* strain TN. *Bacillus* strain TN cells were grown at 65° C. in 50 ml of TGP medium until the absorbance at 600 nm ($A_{600}$) reached 0.5-0.6. The culture was chilled on ice for 15-30 min. The cells were harvested by centrifugation and washed once in 10 ml and twice in 5 ml of cold TH buffer (272 mM trehalose and 8 mM HEPES; pH 7.5 with KOH). The cell pellet was re-suspended in 400 μl of TH buffer and stored at 4° C. prior to electroporation. Methylated plasmid DNA was used to transform strain TN by electroporation based on a method previously described by Narumi et al (1992) Biotechnology Techniques 6(1). The competent cells were dispensed into 90 μl aliquots and mixed with 2 μl of methylated plasmid DNA (250 ng/μl). The mixture was transferred to cold electroporation cuvettes (0.2 cm electrode gap) and incubated on ice for 5 minutes. The suspensions were then subjected to a 2.5 kV discharge from a 25 μF capacitor and the pulse control was set at 201 ohms (time constant, $\tau=5$ ms) using a EquiBio EasyJect electroporator. The cells were immediately transferred to 5 ml of pre-warmed TGP, incubated at 52° C. for 1 hr, and plated on TGP agar (10 μg/ml kanamycin). The plates were incubated for 24-48 hours at 52° C.

Selection of Recombinants

The following method was used to select for chromosomal integration of the temperature sensitive plasmid pUBUC-IE by homologous recombination.

1. Transformants were grown in 5 ml of TGP (kanamycin) medium at 52° C. for 24 hours.
2. 50 ml of fresh TGP (kanamycin) medium was inoculated with 1 ml from O/N culture and incubated in a shaking water bath at 52° C. until a $OD_{600}$ was reached ~0.5.
3. 15 ml of the above culture was centrifuged at 4100 rpm for 5 min at 5° C. and the pellet was resuspended in 150 μl of TGP (10:g/ml kanamycin) medium and spread on TGP (kanamycin) plates.
4. The plates were incubated at 68° C. for 16 hours.
5. The isolated colonies were picked and analysed for plasmid integration into the insertion sequence site by PCR.

Screening of TN Integrants

TN integrants were isolated at 68° C. Failure to amplify a PCR product using LDH primers in TN integrants indicated that at least one copy of plasmid pUBUC-IE had become integrated into the chromosome. As a result of integration the new strain TN-T9 was found to be more stable with regard to ldh reversion and "take over" than the parental strain TN.

Stability of Strain TN-T9

The fermentation was run under sub-optimal conditions such that residual sugar was present in the medium; conditions which favour reversion. The fermentation ran continuously for over 750 hours without any trace of lactate production despite residual sugar, pyruvate excretion and numerous deviations from the set conditions. Ethanol was produced in relatively large amounts throughout the fermentation. Kanamycin was not used to select for integrants throughout the entire fermentation. These results indicate that the ldh gene mutation in TN-T9 is stable in continuous culture under the experimental conditions (pH 7.0, 65° C. with a 2% sugar feed).

Ethanol Yields and Productivity

The fermentation conditions have been optimised for ethanol production from glucose, xylose and glucose/xylose based feedstocks.

Culture type: continuous
Temperature: 65° C.
pH: 6.8
Sugar concentration in feed: 2-10%
Sparge gas: air
Redox: >−350 mV (controlled through air flow rate)
Dilution rate: 0.36-0.6 $h^{-1}$ Under these conditions the ethanol yields obtained were between 0.4-0.5 g/g sugar. Ethanol productivities, using a dilution rate of 0.5 $h^{-}$, were approximately 4 and 8 g ethanol/litre/hour on 2 and 4% sugar feeds, respectively.

Example 2

Selection of the Kanamycin Sensitive Strain

TN-TK

*Bacillus* TN-TK is a kanamycin sensitive derivative of TN-T9. This strain is completely stable with regard to the ldh mutation and an ideal host for plasmid borne expression involving kanamycin as a selectable marker.

TN-T9 was first grown at 68° C. for 24 hours in 5 ml of TGP supplemented with kanamycin (10 μg/ml). Approximately 100 ml of culture was spread on two TGP (Km) agar plates and incubated overnight at 68° C. Several hundred colonies were obtained and 100 were transferred to fresh TGP (Km) plates using a sterile toothpick. After overnight growth at 68° C., the colonies were transferred (by replica plating) to fresh TGP plates and TGP (Kin) plates and grown overnight at 68 C.

Two kanamycin sensitive colonies were obtained on TGP but not on the corresponding TGP (Km) plate. The ldh gene regions from these colonies were amplified by PCR and found to be comparable in size to the disrupted ldh gene from TN-T9 (parental strain). PCR was used to demonstrate that the strains had lost the gene conferring resistance to kanamycin. One derivative referred to as TN-TK was chosen for further growth experiments. These experiments confirmed that the kanamycin sensitivity and ldh mutation were completely stable.

The invention claimed is:

1. A method of stabilizing a mutation, wherein the mutation comprises insertion of a first insertion element in an ldh (lactate dehydrogenase) gene of a *Bacillus* sp., comprising:
   integrating plasmid DNA into the first insertion element within the ldh gene by homologous recombination, wherein the plasmid DNA comprises an artificial operon encoding pyruvate decarboxylase (PDC) and alcohol dehydrogenase (ADH) operatively linked to a second insertion element.

2. The method according to claim 1 wherein both insertion elements comprise nucleotides 651-3800 of SEQ ID NO:1.

3. The method according to claim 1 wherein the plasmid DNA comprises a gene encoding a pyruvate decarboxylase from a *Zymomonas* sp.

4. The method according to claim 3 wherein the plasmid DNA comprises a gene encoding a pyruvate decarboxylase from *Zymomonas mobilis*.

5. The method according to claim 1 wherein the *Bacillus* sp, is *Bacillus* strain LN.

6. The method according to claim 1 wherein the plasmid DNA stably integrates into the chromosome of the *Bacillus* sp.

7. The method according to claim 1 wherein the plasmid DNA is a shuttle vector which is able to replicate in *E. coli* and *Bacillus* strains.

* * * * *

SEQUENCE LISTING

<160> NUMBER OF SEQ ID NOS: 16

<210> SEQ ID NO 1
<211> LENGTH: 4913
<212> TYPE: DNA
<213> ORGANISM: Bacillus strain TN
<220> FEATURE:
<221> NAME/KEY: misc_feature
<222> LOCATION: (1)...(4913)
<223> OTHER INFORMATION: n = A,T,C or G

<400> SEQUENCE: 1

```
agggcaatct gaaaggaagg gaaaattcct ttcggattgt cctttagtt attttatgg      60
ggagtgaata ttatataggc attacggaaa tgataatggc agagtttttt catttattag    120
actgcttgat gtaattggat gtgatgatac aaaaataatg ttgtgtaaac aaaatgttaa    180
caaaaaagac aaatttcatt catagttgat acttgataaa gattgtgaaa taatgcacaa    240
tatatcaatg tatgagcagt ttcacaaatt cattttttgg aaaggatgac agacagcgat    300
gaaacaacaa ggcatgaatc gagtagcact tataggaacg gggttcgttg gggcagcta    360
tgcatttgcc cttatgaacc aaggaatagc agatgagtta gtattgattg atgtaaataa    420
gaataaggca gagggcgatg tgatggattt aatcacggaa aagtattcgc gccgaagccg    480
atgaatattt ggtttggaga ttatcaagat tgccaagacg ccgatttggt ggtgatttgt    540
gcagggctaa ccaaaagcc gggagaaaca agactggatc ttgttgacaa aaatattaat    600
atcttcaaaa cgattgtcga ttctgtgatg aaatccggat ttgatggcgt tangtcttgt    660
tgtaaattat cactttattt ccgcacaaaa aagactcttt tttgcacatt ccttcggaat    720
atccctctcc cccttttccga aagaatgtgc taaattttt gtgaattatt tcggaatggg    780
acatgggtga tttccagagg ggggacgagg acgtgattcg gtttcatgac tttcaggtcg    840
atgtccagac atatgcccag cggggaaaac aaaacgactt tccccttctt aagcggtgcc    900
ctcattgcca ggcaaaacgc cctctttatc gccatgggta ctacgaacga aatgccgtga    960
cgtcgcatca gtcttatcgc atttggatcg ctcggtatcg ctgcccggag tgcaggagga   1020
cggtggccgt gttgccttca tttcttctcc cttattttca gtatacgttg cccaccatat   1080
ggagagtggt gaaagaacgg ttgggcctga ctccgaaacg ggggatggag gaggctccac   1140
tccttcctac ggatgaaggg gtttatttt atgtcccgac gtttattccg aaatttgaac   1200
caccttcatt ggttttttgc ggagcgctgg gagaaaaatt ggtcctgcca tcgcccaagc   1260
cgagagaacg agccctatgg tggatccaga cgatggagga gatcggcctc ttttcgtca   1320
tccaagagat atgggagcac cgatcgacgc atcttttgc acgtacattc agttcctgat   1380
ttacttatat ccccttatat ggaatcattt atagattccc aaacctttcc tctcgacggt   1440
cgggggaatg atccgatagg atagagacag gatggaccga taaggtccta gaatgggatg   1500
aacgaaggag gagatcgaaa tgaatgagtc gatgagacag gagatcgctt tatttcggta   1560
tggattgatc gctccattgg tgaatggaca agtcgatcca aaaacgtact tgaaggaagt   1620
agcggaacgg atccatcaag ttccccacca tggagagaaa cgcatcgccg ccaaaacgat   1680
cctcgactgg tgcacgcagt acaaaaaagg gggctttgag gcgctgaagc cgaaacgacg   1740
gtcggaccgt ggccattccc ggaggctgtc acctgaagaa gaggatcaca ttttagccct   1800
gagaaaaaaa cacccccaca tgcccgtgac ggtgttttac caacacctta tcgagcaggg   1860
ggaaatccaa tccatctctt atttcactat ataccgactt ttaaaaaaat acaacctcgt   1920
```

-continued

```
ggggaaagaa attttaccga ttcctgaacg aaaacgattc gcgtacgatc aggtcaatga      1980
gctctggcaa ggtgatttgt cccatggccc gttgattcgc gtgaatggca aaacgcaaaa      2040 aacgttttg attgcctata tcgatgactg ctcgcgggtc gtgccgtacg ctcagttttt       2100
ctcttccgag aaatttgacg ggttgcggat cgtaaccaag gaagcgctgc ttcgatacgg      2160
aaagccgaag cgaatttact cggataacgg caagatttat cgggcggaac ccttgcagta     2220
cgcctgcgcg gagttaggga tcaccttgat ccatacccag ccgtacgatc cgcaaagcaa     2280
agggaaaatc gaacgatttt tccgcaccgt acagacgcgg ttttacccgt tgctcgaaat     2340
gaattcaccg aagtcgctcg aagagctaaa cgagcgattt tggaagtggt tggaggaaga    2400
ttaccatcga aaaccgcatg cctcgttgaa cgggaagacg ccacatgaag tgtttcaatc    2460
gcaagtccat ttggtgtcgt tcgtcgagga ttcggattgg ctcgactcga tctttttgaa    2520
acgcgaatac cgtaaagtga aggccgatgg tacggtcacg ttgaacaagc agctgtatga    2580
agttccgccc cggttcatcg gacaatcgat cgaactccgt tatgatgaac aaggcgtgta    2640
tgtgtacgaa gacggtcaac gggtcgccga agcggtcctt gttcgcttcg aggacaatgc    2700
ctatgtgaaa cgccatcggt caccgtttgc ggcggttccg gtagagggag gcgaaaacga    2760
tgtataaaac gttttattcc ctttcccgag agccgttttc gaaggagacg aatccaccag    2820
aggcttatca aggggcctcg tatcaagagg ccctcgccgc tttggactac gtgaaacgaa    2880
caagagggat cgggctattg atcggtgaac caggggccgg caagacattc gcccttcggg    2940
cgtttaagga tccctgaat ccgtcactgt atcacgtcgt ttattttcca ttgtcaacgg     3000
gaagcgtgat ggacttttat cgcggccttg ccttcgggct cggggaagag ccgaaatacc    3060
gcaaggtcga cttgttttat caaatccaac aagggatcga gcgcttgtat catgaacaac    3120
gggtaacgtc agtgttcatc ctcgatgaaa tgcatttagc gaaggatgcc tttctgcagg    3180
atatcgcgat cctgttcaac tttcacatgg actcaacaaa tccgtttgtc ttgattttgg    3240
cggggctgcc ccatttacag gcaaaactac ggttgaaatc aacaccgtcc gcttcaccaa    3300
cgaatcatca tgcgatacca gatggggcct cttgataagg aagaagtggt aggatatatc   3360
gaacaccgct gaaacaggcg ggggcgaaac acccgatttt taccccagct gccttagaag    3420
cgatcgccct gcagtcgcag gggtggccgc ggatcatcaa caacctcgcc accacttgcc    3480
tgttatacgg cgctcaatta aaaaaacata tgattgacga agacattgtg cgtatggcag    3540
ccgaagaaat ggggtactga cacagcaggg gctgatcggc ccctgttatg tttcatcccg    3600
atccatcctc attctagtta atcatccgaa ataatgtgca aatgttcgga ataatctgc    3660 aaaacctgga ataattcgca aagattttgc acattatttc cgaatccgtc cgaaataatt    3720
tgaaaaaggg attctgaaat aatgtgctaa tttacatttc ttgtggcaac gaacccagtg    3780 gatatttaa cgtatgctac ttggaaattt agcgggttac cgaaagagcg ggtaatcggc     3840
tcaggaacga ttcttgatac agcaagattc cgcttcttgc taagtgaata ttttcaagtg    3900
gctccgacca atgtacatgc gtatattatt ggcgagcatg gggatacaga gctgcctgtt   3960
tggagccatg cggaaattgg aagcattcca gttgagcaaa tattgatgca aaacgataac   4020
tatagaaaag aggatttaga caatatcttt gttaatgttc gtgatgcggc atatcaaatc    4080
attgagaaaa aaggggcaac gtattacggc attgcaatgg gattagtccg tatcactcgt    4140
gctattttgc acaatgaaaa tgccatctta accgtttctg ctcatttgga cggccaatat    4200
ggcgaacgaa atgtttatat tggcgtgcct gccattatca accgaaacgg tattcgtgaa    4260
gtgatggaat tgacgctaaa tgaaacagaa caacaacaat tccatcatag tgtaactgta    4320
```

```
ttaaaagaca ttctttcccg ttattttgat gatgtaaaat aatactgact ttgaatacaa    4380
caaggtgaac atcgtgtgga tacaacatta caatcccttg cataacacat atctttcggc    4440
atttattgcg gcgtttccga tcgtttattt tctattatgc ttaactgtgt ttaggatgag    4500
gggagtaaaa gccgcttttc tcattccttg ttttggttta gtaacagctg ttttgttttt    4560
ccatatgccg atttcaaagg cgattgctgc gtccgtctat ggaatcgcaa acggtttatg    4620
gccgattggc tatattgtga ttatggccgt ctggctgtat aaaattgctg tgaaaacggg    4680
gaaatttgat attatccgca gcagtattgc aaacatttcg gaggatcagc ggcttcaact    4740
gctgctcatc ggctttagct ttaatgcttt tttagaagga gctgcaggat tcggtgttcc    4800
gattgccatt tcggctgctt tgctttcaga actaggattt catccattaa aagcggccgc    4860
gctttgctta attgccaatg ctgcctctgg cgcgtttgga gcgataggaa ttc          4913

<210> SEQ ID NO 2
<211> LENGTH: 1255
<212> TYPE: DNA
<213> ORGANISM: Bacillus LN

<400> SEQUENCE: 2
agggcaatct gaaaggaagg gaaaattcct ttcggattgt cctttagtt attttatgg      60 ggagtgaata ttatataggc attacggaaa tgataatggc agagtttttt catttattag    120
actgcttgat gtaattggat gtgatgatac aaaaataatg ttgtgtaaac aaaatgttaa    180
caaaaaagac aaatttcatt catagttgat acttgataaa gattgtgaaa taatgcacaa    240
tatatcaatg tatgagcagt ttcacaaatt catttttgg aaaggatgac agacagcgat     300
gaaacaacaa ggcatgaatc gagtagcact tataggaacg gggttcgttg gggccagcta    360
tgcatttgcc cttatgaacc aaggaatagc agatgagtta gtattgattg atgtaaataa    420
gaataaggca gagggcgatg tgatggattt aaatcacgga aaagtattcg cgccgaagcc    480
gatgaatatt tggtttggag attatcaaga ttgccaagac gccgatttgg tggtgatttg    540
tgcaggggct aaccaaaagc cgggagaaac aagactggat cttgttgaca aaaatattaa    600
tatcttcaaa acgattgtcg attctgtgat gaaatccgga tttgatggcg ttttctttgt    660
ggcaacgaac ccagtggata tttttaacgta tgctacttgg aaatttagcg ggttaccgaa    720
agagcgggta atcggctcag gaacgattct tgatacagca agattccgct tcttgctaag    780
tgaatatttt caagtggctc cgaccaatgt acatgcgtat attattggcg agcatgggga    840
tacagagctg cctgtttgga gccatgcgga aattggaagc attccagttg agcaaatatt    900
gatgcaaaac gataactata gaaaagagga tttagacaat atctttgtta atgttcgtga    960
tgcggcatat caaatcattg agaaaaaagg ggcaacgta tacggcattg caatgggatt    1020
agtccgtatc actcgtgcta ttttgcacaa tgaaaatgcc atcttaaccg tttctgctca    1080
tttggacggc caatatggcg aacgaaatgt ttatattggc gtgcctgcca ttatcaaccg    1140
aaacggtatt cgtgaagtga tggaattgac gctaaatgaa acagaacaac aacaattcca    1200
tcatagtgta actgtattaa aagacattct ttcccgttat tttgatgatg taaaa         1255

<210> SEQ ID NO 3
<211> LENGTH: 319
<212> TYPE: PRT
<213> ORGANISM: Bacillus LN

<400> SEQUENCE: 3

Met Lys Gln Gln Gly Met Asn Arg Val Ala Leu Ile Gly Thr Gly Phe
1               5                   10                  15
```

Val Gly Ala Ser Tyr Ala Phe Ala Leu Met Asn Gln Gly Ile Ala Asp
            20                  25                  30

Glu Leu Val Leu Ile Asp Val Asn Lys Asn Lys Ala Glu Gly Asp Val
            35                  40                  45

Met Asp Leu Asn His Gly Lys Val Phe Ala Pro Lys Pro Met Asn Ile
50                  55                  60

Trp Phe Gly Asp Tyr Gln Asp Cys Gln Asp Ala Asp Leu Val Val Ile
65                  70                  75                  80

Cys Ala Gly Ala Asn Gln Lys Pro Gly Glu Thr Arg Leu Asp Leu Val
                85                  90                  95

Asp Lys Asn Ile Asn Ile Phe Lys Thr Ile Val Asp Ser Val Met Lys
            100                 105                 110

Ser Gly Phe Asp Gly Val Phe Leu Val Ala Thr Asn Pro Val Asp Ile
            115                 120                 125

Leu Thr Tyr Ala Thr Trp Lys Phe Ser Gly Leu Pro Lys Glu Arg Val
130                 135                 140

Ile Gly Ser Gly Thr Ile Leu Asp Thr Ala Arg Phe Arg Phe Leu Leu
145                 150                 155                 160

Ser Glu Tyr Phe Gln Val Ala Pro Thr Asn Val His Ala Tyr Ile Ile
                165                 170                 175

Gly Glu His Gly Asp Thr Glu Leu Pro Val Trp Ser His Ala Glu Ile
            180                 185                 190

Gly Ser Ile Pro Val Glu Gln Ile Leu Met Gln Asn Asp Asn Tyr Arg
            195                 200                 205

Lys Glu Asp Leu Asp Asn Ile Phe Val Asn Val Arg Asp Ala Ala Tyr
210                 215                 220

Gln Ile Ile Glu Lys Lys Gly Ala Thr Tyr Tyr Gly Ile Ala Met Gly
225                 230                 235                 240

Leu Val Arg Ile Thr Arg Ala Ile Leu His Asn Glu Asn Ala Ile Leu
                245                 250                 255

Thr Val Ser Ala His Leu Asp Gly Gln Tyr Gly Glu Arg Asn Val Tyr
            260                 265                 270

Ile Gly Val Pro Ala Ile Ile Asn Arg Asn Gly Ile Arg Glu Val Met
            275                 280                 285

Glu Leu Thr Leu Asn Glu Thr Glu Gln Gln Phe His His Ser Val
290                 295                 300

Thr Val Leu Lys Asp Ile Leu Ser Arg Tyr Phe Asp Asp Val Lys
305                 310                 315

<210> SEQ ID NO 4
<211> LENGTH: 528
<212> TYPE: DNA
<213> ORGANISM: Bacillus LN

<400> SEQUENCE: 4
gtgaacatcg tgtggataca acattacaat cccttgcata acacatatct ttcggcattt      60
attgcggcgt ttccgatcgt tttatttcta ttatgcttaa ctgtgtttag gatgagggga     120
gtaaaagccg cttttctcat tctttgtttt ggtttagtaa cagctgtttt gttttttccat    180 atgccgattt caaggcgat tgctgcgtcc gtctatggaa tcgcaaacgg tttatggccg      240
attggctata ttgtgattat ggccgtctgg ctgtataaaa ttgctgtgaa acgggggaaa     300
tttgatatta tccgcagcag tattgcaaac atttcggagg atcagcggct tcaactgctg    360
ctcatcggct ttagctttaa tgcttttttta gaaggagctg caggattcgg tgttccgatt     420

```
gccatttcgg ctgctttgct ttcagaacta ggatttcatc cattaaaagc ggccgcgctt      480
tgcttaattg ccaatgctgc ctctggcgcg tttggagcga taggaatt                  528
```

<210> SEQ ID NO 5
<211> LENGTH: 176
<212> TYPE: PRT
<213> ORGANISM: Bacillus LN

<400> SEQUENCE: 5

```
Val Asn Ile Val Trp Ile Gln His Tyr Asn Pro Leu His Asn Thr Tyr
 1               5                  10                  15

Leu Ser Ala Phe Ile Ala Ala Phe Pro Ile Val Leu Phe Leu Leu Cys
            20                  25                  30

Leu Thr Val Phe Arg Met Arg Gly Val Lys Ala Ala Phe Leu Ile Leu
        35                  40                  45

Cys Phe Gly Leu Val Thr Ala Val Leu Phe Phe His Met Pro Ile Ser
 50                  55                  60

Lys Ala Ile Ala Ala Ser Val Tyr Gly Ile Ala Asn G

-continued

```
gatgaaaaag gcggagaaaa atgcaaatac agcttgaaag acatcatcag tgcgtggtcc      900
ccgttttata ttttaacggt gctcgttatt atatggagtc tgcctggttt taaagctctg      960
tttgccgagg gaggcgcact gcagcgaacg acgcttttgt ttaaggtgcc attttttgcat   1020 ggcgaagtcg cgaaaattcc tccggtggcg ccggcccaga cggcattaga tgccatattt   1080
aagctagacc ttgtatcggc aacaggcacg gcgattttac tggcggtgct gttcacaggg   1140
atgtttagca aaacattac gttcgcggaa ggaatacaaa gtttaaaaga acatgtaaa     1200 gagctattca ttcctgtatt aacgatttgt tttatcatgg gatttgccaa cttagccgac   1260
tatgcaggtt tatccgctgc gattggtttg gcattggcgg agacaggcga tgcatttcca   1320
tttgtttccc cgttattagg gtggcttggt gtgtttatta caggatctgt cgtgagcaat   1380
aatgctttat tcggccattt acaagctgtt acaggagcgc aaataggac aagctcttcg    1440 ttattgcttg cggctaacac cagcggggga gtgatgggga aacttatttc cccgcagtcc   1500
atcgccatag caactgctgc agtgaaagag acaggcaaag aatctcacct gtttaaaatg   1560
acgatttatt atagcttgat cctgctattg tttgtgggag tatggacgta ctttctttcg   1620
accgcaggaa tgtagatcat tatggtttgt tattcagtta ggcaccgtgt ataaatgaaa   1680
aaagatgtat tttgcggcct tttc                                            1704
```

<210> SEQ ID NO 7
<211> LENGTH: 566
<212> TYPE: PRT
<213> ORGANISM: Bacillus LN

<400> SEQUENCE: 7

```
Val Asn Ile Val Trp Ile Gln His Tyr Asn Pro Leu His Asn Thr Tyr
  1               5                  10                  15

Leu Ser Ala Phe Ile Ala Ala Phe Pro Ile Val Leu Phe Leu Leu Cys
             20                  25                  30

Leu Thr Val Phe Arg Met Arg Gly Val Lys Ala Ala Phe Leu Ile Leu
         35                  40                  45

Cys Phe Gly Leu Val Thr Ala Val Leu Phe Phe His Met Pro Ile Ser
     50                  55                  60

Lys Ala Ile Ala Ala Ser Val Tyr Gly Ile Ala Asn Gly Leu Trp Pro
 65                  70                  75                  80

Ile Gly Tyr Ile Val Ile Met Ala Val Trp Leu Tyr Lys Ile Ala Val
                 85                  90                  95

Lys Thr Gly Lys Phe Asp Ile Ile Arg Ser Ser Ile Ala Asn Ile Ser
            100                 105                 110

Glu Asp Gln Arg Leu Gln Leu Leu Leu Ile Gly Phe Ser Phe Asn Ala
        115                 120                 125

Phe Leu Glu Gly Ala Ala Gly Phe Gly Val Pro Ile Ala Ile Ser Ala
    130                 135                 140

Ala Leu Leu Ser Glu Leu Gly Phe His Pro Leu Lys Ala Ala Ala Leu
145                 150                 155                 160

Cys Leu Ile Ala Asn Ala Ala Ser Gly Ala Phe Gly Ala Ile Gly Ile
                165                 170                 175

Pro Val Ile Val Gly Ala Gln Met Gly Asp Leu Thr Pro Ile Glu Leu
            180                 185                 190

Ser Arg Thr Leu Ala Trp Ile Leu Pro Phe Ile Ser Phe Leu Ile Pro
        195                 200                 205

Phe Leu Leu Val Phe Val Leu Asp Lys Trp Lys Gly Ile Lys Glu Thr
    210                 215                 220
```

| | | | | | | | | | | | | |
|---|---|---|---|---|---|---|---|---|---|---|---|---|
| Leu | Pro | Ala | Leu | Phe | Val | Val | Ser | Gly | Ser | Tyr | Thr | Ile | Val | Gln | Thr |
| 225 | | | | 230 | | | | | 235 | | | | | 240 | |
| Leu | Thr | Ile | Ile | Val | Leu | Gly | Pro | Glu | Leu | Ala | Asn | Ile | Leu | Ala | Ala |
| | | | | 245 | | | | | 250 | | | | | 255 | |
| Leu | Val | Ser | Met | Gly | Ala | Leu | Ala | Leu | Phe | Leu | Arg | Lys | Trp | Gln | Pro |
| | | | 260 | | | | | 265 | | | | | 270 | | |
| Ser | Asn | Ile | Tyr | Arg | Val | Asn | Pro | Asp | Glu | Lys | Gly | Glu | Lys | Cys |
| | | 275 | | | | | 280 | | | | | 285 | | |
| Lys | Tyr | Ser | Leu | Lys | Asp | Ile | Ile | Ser | Ala | Trp | Ser | Pro | Phe | Tyr | Ile |
| | 290 | | | | | 295 | | | | | 300 | | | | |
| Leu | Thr | Val | Leu | Val | Ile | Ile | Trp | Ser | Leu | Pro | Gly | Phe | Lys | Ala | Leu |
| 305 | | | | | 310 | | | | | 315 | | | | | 320 |
| Phe | Ala | Glu | Gly | Gly | Ala | Leu | Gln | Arg | Thr | Thr | Leu | Leu | Phe | Lys | Val |
| | | | | 325 | | | | | 330 | | | | | 335 | |
| Pro | Phe | Leu | His | Gly | Glu | Val | Ala | Lys | Ile | Pro | Pro | Val | Ala | Pro | Ala |
| | | | 340 | | | | | 345 | | | | | 350 | | |
| Gln | Thr | Ala | Leu | Asp | Ala | Ile | Phe | Lys | Leu | Asp | Leu | Val | Ser | Ala | Thr |
| | | 355 | | | | | 360 | | | | | 365 | | | |
| Gly | Thr | Ala | Ile | Leu | Leu | Ala | Val | Leu | Phe | Thr | Gly | Met | Phe | Ser | Lys |
| 370 | | | | | 375 | | | | | 380 | | | | | |
| Asn | Ile | Thr | Phe | Ala | Glu | Gly | Ile | Gln | Ser | Leu | Lys | Glu | Thr | Cys | Lys |
| 385 | | | | | 390 | | | | | 395 | | | | | 400 |
| Glu | Leu | Phe | Ile | Pro | Val | Leu | Thr | Ile | Cys | Phe | Ile | Met | Gly | Phe | Ala |
| | | | | 405 | | | | | 410 | | | | | 415 | |
| Asn | Leu | Ala | Asp | Tyr | Ala | Gly | Leu | Ser | Ala | Ala | Ile | Gly | Leu | Ala | Leu |
| | | | 420 | | | | | 425 | | | | | 430 | | |
| Ala | Glu | Thr | Gly | Asp | Ala | Phe | Pro | Phe | Val | Ser | Pro | Leu | Leu | Gly | Trp |
| | | | 435 | | | | | 440 | | | | | 445 | | |
| Leu | Gly | Val | Phe | Ile | Thr | Gly | Ser | Val | Val | Ser | Asn | Asn | Ala | Leu | Phe |
| | 450 | | | | | 455 | | | | | 460 | | | | |
| Gly | His | Leu | Gln | Ala | Val | Thr | Gly | Ala | Gln | Ile | Gly | Thr | Ser | Ser | Ser |
| 465 | | | | | 470 | | | | | 475 | | | | | 480 |
| Leu | Leu | Leu | Ala | Ala | Asn | Thr | Ser | Gly | Gly | Val | Met | Gly | Lys | Leu | Ile |
| | | | | 485 | | | | | 490 | | | | | 495 | |
| Ser | Pro | Gln | Ser | Ile | Ala | Ile | Ala | Thr | Ala | Ala | Val | Lys | Glu | Thr | Gly |
| | | | | 500 | | | | | 505 | | | | | 510 | |
| Lys | Glu | Ser | His | Leu | Phe | Lys | Met | Thr | Ile | Tyr | Tyr | Ser | Leu | Ile | Leu |
| | | | 515 | | | | | 520 | | | | | 525 | | |
| Leu | Leu | Phe | Val | Gly | Val | Trp | Thr | Tyr | Phe | Leu | Ser | Thr | Ala | Gly | Met |
| 530 | | | | | 535 | | | | | 540 | | | | | |
| Ile | Ile | Met | Val | Cys | Tyr | Ser | Val | Arg | His | Arg | Val | Met | Lys | Lys | Asp |
| 545 | | | | | 550 | | | | | 555 | | | | | 560 |
| Val | Phe | Cys | Gly | Leu | Phe |
| | | | | 565 | |

<210> SEQ ID NO 8
<211> LENGTH: 1573
<212> TYPE: DNA
<213> ORGANISM: Bacillus LN

<400> SEQUENCE: 8

```
gtggctccaa gctatgtatt tttagcaagc gaagaggcat cctatattac ggggcaaatg      60
atacatgtga atgcggaaaa gattgtcaat ggatagaaag cggcggaaaa cggaacgttc     120
ttcatgactg cgcaaatttt atgtaatatt ttctgacata gttgttgtgc ggtctgtata     180
```

-continued

```
tcaccgttat gataaaaata catgctattt cttatccatg ttcctcaacc ttttgtatgg    240
attgcaaaag gcatcctctc ttccttcact tgcaacaatt tattgcaagt ttttgtgtat    300
ttaggaatat tatatgccgc atcaacggac aggcaatgtg aacaaagctg ctccaaacat    360
aacatattat tgatatttct tgaaatatta ctaatatttt gattaaatgt ttttgtttgc    420
actgcagctt ttacaaaagt agaatatttt atggtgttta tccgaagaat atcatcatga    480 tacccctatgg gagggaattg tgatgaaagc tgcagtagta gagcaattta aggaaccatt    540
aaaaattaaa gaagtggaaa agccatccat ttcatatggc gaagtattag tccgcattaa    600
agcatgcggt gtatgccata cggacttgca tgccgctcac ggcgattggc cagtaaaacc    660
aaaacttcct ttaatccctg gccatgaagg agtcggaatt gttgaagaag tcggtccggg    720
ggtaacccat ttaaaagtgg agaccgcgt tggaattcct tggttatatt ctgcttgcgg    780
ccattgcgaa tattgtttaa gcggacaaga gacattatgt gaacatcaag aaaacgccgg    840
ctactcagtc gacgggggt atgcagaata ttgcagagct gcggcagact atgtggtgaa    900
aattcctgac aacttgtcgt ttgaagaagc tgctcctatt ttctgcgccg gagttactac    960
ttataaagcg ttaaaagtca caggtacaaa accgggagaa tgggtagcga tctatggcat    1020
cggtggcctt ggacatgttg ccgtccagta tgcgaaagcg atgggcttc atgttgttgc    1080 agtggatatc ggcgatgaga aactggaact tgcaaaagag cttggcgccg atcttgttgt    1140
aaatcctgca aagaaaatg cggcacaatt tatgaaagag aaagtcggcg gagtacacgc    1200
ggctgttgtg acagctgtat ctaaacctgc ttttcaatct gcgtacaatt ctgtccgcag    1260
aggcggcacg tgcgtgcttg tcggattacc gccggaagaa atgcctattc caatctttga    1320
tacggtatta aacggaatta aaattatcgg ttccattgtc ggcacgcgga agacttgca    1380 agaagcgctt cagttcgctg cagaaggtaa agtaaaaacc attattgaag tgcaacctct    1440
tgaaaaaatt aacgaagtat ttgacagaat gctaaaagga gaaattaacg acgggttgt    1500 tttaacgtta gaaaataata attaacgtca acaacacaat gttgacaacc cggcattcta    1560
gggctgtctc atc                                                      1573
```

<210> SEQ ID NO 9
<211> LENGTH: 319
<212> TYPE: PRT
<213> ORGANISM: Bacillus strain TN

<400> SEQUENCE: 9

Met Lys Gln Gln Gly Met Asn Arg Val Ala Leu Ile Gly Thr Gly Phe
1               5                   10                  15

Val Gly Ala Ser Tyr Ala Phe Ala Leu Met Asn Gln Gly Ile Ala Asp
                20                  25                  30

Glu Leu Val Leu Ile Asp Val Asn Lys Asn Lys Ala Glu Gly Asp Val
            35                  40                  45

Met Asp Leu Asn His Gly Lys Val Phe Ala Pro Lys Pro Met Asn Ile
        50                  55                  60

Trp Phe Gly Asp Tyr Gln Asp Cys Gln Asp Ala Asp Leu Val Val Ile
65                  70                  75                  80

Cys Ala Gly Ala Asn Gln Lys Pro Gly Glu Thr Arg Leu Asp Leu Val
                85                  90                  95

Asp Lys Asn Ile Asn Ile Phe Lys Thr Ile Val Asp Ser Val Met Lys
            100                 105                 110

Ser Gly Phe Asp Gly Val Phe Leu Val Ala Thr Asn Pro Val Asp Ile
        115                 120                 125

```
Leu Thr Tyr Ala Thr Trp Lys Phe Ser Gly Leu Pro Lys Glu Arg Val
            130                 135                 140

Ile Gly Ser Gly Thr Ile Leu Asp Thr Ala Arg Phe Arg Phe Leu Leu
145                 150                 155                 160

Ser Glu Tyr Phe Gln Val Ala Pro Thr Asn Val His Ala Tyr Ile Ile
                165                 170                 175

Gly Glu His Gly Asp Thr Glu Leu Pro Val Trp Ser His Ala Glu Ile
            180                 185                 190

Gly Ser Ile Pro Val Glu Gln Ile Leu Met Gln Asn Asp Asn Tyr Arg
        195                 200                 205

Lys Glu Asp Leu Asp Asn Ile Phe Val Asn Val Arg Asp Ala Ala Tyr
    210                 215                 220

Gln Ile Ile Glu Lys Lys Gly Ala Thr Tyr Tyr Gly Ile Ala Met Gly
225                 230                 235                 240

Leu Val Arg Ile Thr Arg Ala Ile Leu His Asn Glu Asn Ala Ile Leu
                245                 250                 255

Thr Val Ser Ala His Leu Asp Gly Gln Tyr Gly Glu Arg Asn Val Tyr
            260                 265                 270

Ile Gly Val Pro Ala Ile Ile Asn Arg Asn Gly Ile Arg Glu Val Met
        275                 280                 285

Glu Leu Thr Leu Asn Glu Thr Glu Gln Gln Gln Phe His His Ser Val
    290                 295                 300

Thr Val Leu Lys Asp Ile Leu Ser Arg Tyr Phe Asp Asp Val Lys
305                 310                 315

<210> SEQ ID NO 10
<211> LENGTH: 340
<212> TYPE: PRT
<213> ORGANISM: Bacillus strain TN

<400> SEQUENCE: 10

Met Lys Ala Ala Val Val Glu Gln Phe Lys Glu Pro Leu Lys Ile Lys
1               5                   10                  15

Glu Val Glu Lys Pro Ser Ile Ser Tyr Gly Glu Val Leu Val Arg Ile
            20                  25                  30

Lys Ala Cys Gly Val Cys His Thr Asp Leu His Ala Ala His Gly Asp
        35                  40                  45

Trp Pro Val Lys Pro Lys Leu Pro Leu Ile Pro Gly His Glu Gly Val
    50                  55                  60

Gly Ile Val Glu Glu Val Gly Pro Gly Val Thr His Leu Lys Val Gly
65                  70                  75                  80

Asp Arg Val Gly Ile Pro Trp Leu Tyr Ser Ala Cys Gly His Cys Glu
                85                  90                  95

Tyr Cys Leu Ser Gly Gln Glu Thr Leu Cys Glu His Gln Glu Asn Ala
            100                 105                 110

Gly Tyr Ser Val Asp Gly Gly Tyr Ala Glu Tyr Cys Arg Ala Ala Ala
        115                 120                 125

Asp Tyr Val Val Lys Ile Pro Asp Asn Leu Ser Phe Glu Glu Ala Ala
    130                 135                 140

Pro Ile Phe Cys Ala Gly Val Thr Thr Tyr Lys Ala Leu Lys Val Thr
145                 150                 155                 160

Gly Thr Lys Pro Gly Glu Trp Val Ala Ile Tyr Gly Ile Gly Gly Leu
                165                 170                 175

Gly His Val Ala Val Gln Tyr Ala Lys Ala Met Gly Leu His Val Val
            180                 185                 190
```

```
Ala Val Asp Ile Gly Asp Glu Lys Leu Glu Leu Ala Lys Glu Leu Gly
        195                 200                 205

Ala Asp Leu Val Val Asn Pro Ala Lys Glu Asn Ala Ala Gln Phe Met
        210                 215                 220

Lys Glu Lys Val Gly Val His Ala Ala Val Thr Ala Val Ser
225                 230                 235                 240

Lys Pro Ala Phe Gln Ser Ala Tyr Asn Ser Val Arg Arg Gly Gly Thr
                245                 250                 255

Cys Val Leu Val Gly Leu Pro Pro Glu Glu Met Pro Ile Pro Ile Phe
        260                 265                 270

Asp Thr Val Leu Asn Gly Ile Lys Ile Ile Gly Ser Ile Val Gly Thr
        275                 280                 285

Arg Lys Asp Leu Gln Glu Ala Leu Gln Phe Ala Ala Glu Gly Lys Val
        290                 295                 300

Lys Thr Ile Ile Glu Val Gln Pro Leu Glu Lys Ile Asn Glu Val Phe
305                 310                 315                 320

Asp Arg Met Leu Lys Gly Glu Ile Asn Gly Arg Val Val Leu Thr Leu
                325                 330                 335

Glu Asn Asn Asn
        340

<210> SEQ ID NO 11
<211> LENGTH: 226
<212> TYPE: PRT
<213> ORGANISM: Bacillus

<400> SEQUENCE: 11

Met Gly Asp Phe Gln Arg Gly Asp Glu Asp Val Ile Arg Phe His Asp
1               5                   10                  15

Phe Gln Val Asp Val Gln Thr Tyr Ala Gln Arg Gly Lys Gln Asn Asp
                20                  25                  30

Phe Pro Leu Leu Lys Arg Cys Pro His Cys Gln Ala Lys Arg Pro Leu
            35                  40                  45

Tyr Arg His Gly Tyr Tyr Glu Arg Asn Ala Val Thr Ser His Gln Ser
    50                  55                  60

Tyr Arg Ile Trp Ile Ala Arg Tyr Arg Cys Pro Glu Cys Arg Arg Thr
65                  70                  75                  80

Val Ala Val Leu Pro Ser Phe Leu Pro Tyr Phe Gln Tyr Thr Leu
                85                  90                  95

Pro Thr Ile Trp Arg Val Val Lys Glu Arg Leu Gly Leu Thr Pro Lys
                100                 105                 110

Arg Gly Met Glu Glu Ala Pro Leu Leu Pro Thr Asp Glu Gly Val Leu
            115                 120                 125

Phe Tyr Val Pro Thr Phe Ile Pro Lys Phe Glu Pro Pro Ser Leu Val
        130                 135                 140

Phe Cys Gly Ala Leu Glu Lys Asn Trp Ser Cys His Arg Pro Ser Arg
145                 150                 155                 160

Glu Asn Glu Pro Tyr Gly Gly Ser Arg Arg Trp Arg Ser Ala Ser
                165                 170                 175

Phe Ser Ser Ser Lys Arg Tyr Gly Ser Thr Asp Arg Arg Ile Phe Leu
            180                 185                 190

His Val His Ser Val Pro Asp Leu Leu Ile Ser Pro Tyr Met Glu Ser
        195                 200                 205

Phe Ile Asp Ser Gln Thr Phe Pro Leu Asp Gly Arg Gly Asn Asp Pro
    210                 215                 220
```

```
Ile Gly
225

<210> SEQ ID NO 12
<211> LENGTH: 415
<212> TYPE: PRT
<213> ORGANISM: Bacillus

<400> SEQUENCE: 12

Met Asn Glu Ser Met Arg Gln Glu Ile Ala Leu Phe Arg Tyr Gly Leu
1               5                   10                  15

Ile Ala Pro Leu Val Asn Gly Gln Val Asp Pro Lys Thr Tyr Leu Lys
            20                  25                  30

Glu Val Ala Glu Arg Ile His Gln Val Pro His His Gly Glu Lys Arg
        35                  40                  45

Ile Ala Ala Lys Thr Ile Leu Asp Trp Cys Thr Gln Tyr Lys Lys Gly
    50                  55                  60

Gly Phe Glu Ala Leu Lys Pro Lys Arg Arg Ser Asp Arg Gly His Ser
65                  70                  75                  80

Arg Arg Leu Ser Pro Glu Glu Asp His Ile Leu Ala Leu Arg Lys
                85                  90                  95

Lys His Pro His Met Pro Val Thr Val Phe Tyr Gln His Leu Ile Glu
            100                 105                 110

Gln Gly Glu Ile Gln Ser Ile Ser Tyr Phe Thr Ile Tyr Arg Leu Leu
        115                 120                 125

Lys Lys Tyr Asn Leu Val Gly Lys Glu Ile Leu Pro Ile Pro Glu Arg
    130                 135                 140

Lys Arg Phe Ala Tyr Asp Gln Val Asn Glu Leu Trp Gln Gly Asp Leu
145                 150                 155                 160

Ser His Gly Pro Leu Ile Arg Val Asn Gly Lys Thr Gln Lys Thr Phe
                165                 170                 175

Leu Ile Ala Tyr Ile Asp Asp Cys Ser Arg Val Val Pro Tyr Ala Gln
            180                 185                 190

Phe Phe Ser Ser Glu Lys Phe Asp Gly Leu Arg Ile Val Thr Lys Glu
        195                 200                 205

Ala Leu Leu Arg Tyr Gly Lys Pro Lys Arg Ile Tyr Ser Asp Asn Gly
    210                 215                 220

Lys Ile Tyr Arg Ala Glu Pro Leu Gln Tyr Ala Cys Ala Glu Leu Gly
225                 230                 235                 240

Ile Thr Leu Ile His Thr Gln Pro Tyr Asp Pro Gln Ser Lys Gly Lys
                245                 250                 255

Ile Glu Arg Phe Phe Arg Thr Val Gln Thr Arg Phe Tyr Pro Leu Leu
            260                 265                 270

Glu Met Asn Ser Pro Lys Ser Leu Glu Glu Leu Asn Glu Arg Phe Trp
        275                 280                 285

Lys Trp Leu Glu Glu Asp Tyr His Arg Lys Pro His Ala Ser Leu Asn
    290                 295                 300

Gly Lys Thr Pro His Glu Val Phe Gln Ser Gln Val His Leu Val Ser
305                 310                 315                 320

Phe Val Glu Asp Ser Asp Trp Leu Asp Ser Ile Phe Leu Lys Arg Glu
                325                 330                 335

Tyr Arg Lys Val Lys Ala Asp Gly Thr Val Thr Leu Asn Lys Gln Leu
            340                 345                 350

Tyr Glu Val Pro Pro Arg Phe Ile Gly Gln Ser Ile Glu Leu Arg Tyr
        355                 360                 365
```

```
Asp Glu Gln Gly Val Tyr Val Tyr Glu Asp Gly Gln Arg Val Ala Glu
        370                 375                 380

Ala Val Leu Val Arg Phe Glu Asp Asn Ala Tyr Val Lys Arg His Arg
385                 390                 395                 400

Ser Pro Phe Ala Ala Val Pro Val Glu Gly Gly Glu Asn Asp Val
                405                 410                 415

<210> SEQ ID NO 13
<211> LENGTH: 266
<212> TYPE: PRT
<213> ORGANISM: Bacillus

<400> SEQUENCE: 13

Met Tyr Lys Thr Phe Tyr Ser Leu Ser Arg Glu Pro Phe Ser Lys Glu
1               5                   10                  15

Thr Asn Pro Pro Glu Ala Tyr Gln Gly Ala Ser Tyr Gln Glu Ala Leu
                20                  25                  30

Ala Ala Leu Asp Tyr Val Lys Arg Thr Arg Gly Ile Gly Leu Leu Ile
            35                  40                  45

Gly Glu Pro Gly Ala Gly Lys Thr Phe Ala Leu Arg Ala Phe Lys Glu
50                  55                  60

Ser Leu Asn Pro Ser Leu Tyr His Val Val Tyr Phe Pro Leu Ser Thr
65                  70                  75                  80

Gly Ser Val Met Asp Phe Tyr Arg Gly Leu Ala Phe Gly Leu Gly Glu
                85                  90                  95

Glu Pro Lys Tyr Arg Lys Val Asp Leu Phe Tyr Gln Ile Gln Gln Gly
            100                 105                 110

Ile Glu Arg Leu Tyr His Glu Gln Arg Val Thr Ser Val Phe Ile Leu
        115                 120                 125

Asp Glu Met His Leu Ala Lys Asp Ala Phe Leu Gln Asp Ile Ala Ile
130                 135                 140

Leu Phe Asn Phe His Met Asp Ser Thr Asn Pro Phe Val Leu Ile Leu
145                 150                 155                 160

Ala Gly Leu Pro His Leu Gln Ala Lys Leu Arg Leu Asn Gln His Arg
                165                 170                 175

Pro Leu His Gln Arg Ile Ile Met Arg Tyr Gln Met Gly Pro Leu Asp
            180                 185                 190

Lys Glu Glu Val Val Gly Tyr Ile Glu His Arg Leu Lys Gln Ala Gly
        195                 200                 205

Ala Lys His Pro Ile Phe Thr Pro Ala Ala Leu Glu Ala Ile Ala Leu
210                 215                 220

Gln Ser Gln Gly Trp Pro Arg Ile Ile Asn Asn Leu Ala Thr Thr Cys
225                 230                 235                 240

Leu Leu Tyr Gly Ala Gln Leu Lys Lys His Met Ile Asp Glu Asp Ile
                245                 250                 255

Val Arg Met Ala Ala Glu Glu Met Gly Tyr
            260                 265

<210> SEQ ID NO 14
<211> LENGTH: 27
<212> TYPE: DNA
<213> ORGANISM: Bacilllus

<400> SEQUENCE: 14
aagcttgatg aaatccggat ttgatgg                                    27
```

<210> SEQ ID NO 15
<211> LENGTH: 24
<212> TYPE: DNA
<213> ORGANISM: Bacillus

<400> SEQUENCE: 15
tctagagcta aatttccaag tagc                                          24

<210> SEQ ID NO 16
<211> LENGTH: 3149
<212> TYPE: DNA
<213> ORGANISM: Bacillus strain TN
<220> FEATURE:
<221> NAME/KEY: misc_feature
<222> LOCATION: (1)...(3149)
<223> OTHER INFORMATION: n = A,T,C or G

<400> SEQUENCE: 16

```
angtcttgtt gtaaattatc actttatttc cgcacaaaaa agactctttt ttgcacattc      60
cttcggaata tccctctccc cctttccgaa agaatgtgct aaatttttg tgaattattt     120
cggaatggga catgggtgat ttccagaggg gggacgagga cgtgattcgg tttcatgact     180
ttcaggtcga tgtccagaca tatgcccagc ggggaaaaca aaacgacttt ccccttctta     240
agcggtgccc tcattgccag gcaaaacgcc ctctttatcg ccatgggtac tacgaacgaa     300
atgccgtgac gtcgcatcag tcttatcgca tttggatcgc tcggtatcgc tgcccggagt     360
gcaggaggac ggtggccgtg ttgccttcat ttcttctccc ttattttcag tatacgttgc     420
ccaccatatg gagagtggtg aaagaacggt tgggcctgac tccgaaacgg gggatggagg     480
aggctccact ccttcctacg gatgaagggg ttttatttta tgtcccgacg tttattccga     540
aatttgaacc accttcattg gttttttgcg gagcgctggg agaaaaattg gtcctgccat     600
cgcccaagcc gagagaacga gccctatggt ggatccagac gatggaggag atcggcctct     660
ttttcgtcat ccaagagata tgggagcacc gatcgacgca tcttttttgca cgtacattca     720
gttcctgatt tacttatatc cccttatatg gaatcattta tagattccca aacctttcct     780
ctcgacggtc gggggaatga tccgatagga tagagacagg atggaccgat aaggtcctag     840
aatgggatga acgaaggagg agatcgaaat gaatgagtcg atgagacagg agatcgcttt     900
atttcggtat ggattgatcg ctccattggt gaatggacaa gtcgatccaa aaacgtactt     960
gaaggaagta gcggaacgga tccatcaagt tccccaccat ggagagaaac gcatcgccgc    1020
caaaacgatc ctcgactggt gcacgcagta caaaaagggg ggctttgagg cgctgaagcc    1080
gaaacgacgg tcggaccgtg gccattcccg gaggctgtca cctgaagaag aggatcacat    1140
tttagccctg agaaaaaaac accccacat gcccgtgacg tgttttacc aacacccttat    1200
cgagcagggg gaaatccaat ccatctctta tttcactata taccgacttt taaaaaaata    1260
caacctcgtg gggaaagaaa ttttaccgat tcctgaacga aaacgattcg cgtacgatca    1320
ggtcaatgag ctctggcaag gtgatttgtc ccatggcccg ttgattcgcg tgaatggcaa    1380
aacgcaaaaa acgttttga ttgcctatat cgatgactgc tcgcgggtcg tgccgtacgc    1440
tcagttttc tcttccgaga aatttgacgg gttgcggatc gtaaccaagg aagcgctgct    1500
tcgatacgga aagccgaagc gaatttactc ggataacggc aagatttatc gggcggaacc    1560
cttgcagtac gcctgcgcgg agttaggat caccttgatc catacccagc cgtacgatcc    1620
gcaaagcaaa gggaaaatcg aacgattttt ccgcaccgta cagacgcggt tttacccgtt    1680
gctcgaaatg aattcaccga agtcgctcga agagctaaac gagcgatttt ggaagtggtt    1740
ggaggaagat taccatcgaa aaccgcatgc ctcgttgaac gggaagacgc cacatgaagt    1800
```

-continued

```
gtttcaatcg caagtccatt tggtgtcgtt cgtcgaggat tcggattggc tcgactcgat   1860 cttttttgaaa cgcgaatacc gtaaagtgaa ggccgatggt acggtcacgt tgaacaagca   1920
gctgtatgaa gttccgcccc ggttcatcgg acaatcgatc gaactccgtt atgatgaaca   1980
aggcgtgtat gtgtacgaag acggtcaacg ggtcgccgaa gcggtccttg ttcgcttcga   2040
ggacaatgcc tatgtgaaac gccatcggtc accgtttgcg gcggttccgg tagagggagg   2100
cgaaaacgat gtataaaacg ttttattccc ttttcccgaga gccgttttcg aaggagacga   2160
atccaccaga ggcttatcaa ggggcctcgt atcaagaggc cctcgccgct ttggactacg   2220
tgaaacgaac aagagggatc gggctattga tcggtgaacc aggggccggc aagacattcg   2280
cccttcgggc gtttaaggaa tccctgaatc cgtcactgta tcacgtcgtt tattttccat   2340
tgtcaacggg aagcgtgatg gacttttatc gcggccttgc cttcgggctc ggggaagagc   2400
cgaaataccg caaggtcgac ttgttttatc aaatccaaca agggatcgag cgcttgtatc   2460
atgaacaacg ggtaacgtca gtgttcatcc tcgatgaaat gcatttagcg aaggatgcct   2520
ttctgcagga tatcgcgatc ctgttcaact ttcacatgga ctcaacaaat ccgtttgtct   2580
tgattttggc ggggctgccc catttacagg caaaactacg gttgaaatca acaccgtccg   2640
cttcaccaac gaatcatcat gcgataccag atggggcctc ttgataagga agaagtggta   2700
ggatatatcg aacaccgctg aaacaggcgg gggcgaaaca cccgatttt accccagctg   2760 ccttagaagc gatcgccctg cagtcgcagg ggtggccgcg gatcatcaac aacctcgcca   2820
ccacttgcct gttatacggc gctcaattaa aaaaacatat gattgacgaa gacattgtgc   2880
gtatggcagc cgaagaaatg gggtactgac acagcagggg ctgatcggcc cctgttatgt   2940
ttcatcccga tccatcctca ttctagttaa tcatccgaaa taatgtgcaa atgttcggaa   3000
ataatctgca aaacctggaa taattcgcaa agattttgca cattatttcc gaatccgtcc   3060
gaaataattt gaaaaaggga ttctgaaata atgtgctaat ttacatttct tgtggcaacg   3120
aacccagtgg atattttaac gtatgctac                                    3149
```